US 9,206,357 B2

(12) United States Patent
Hamilon et al.

(10) Patent No.: US 9,206,357 B2
(45) Date of Patent: Dec. 8, 2015

(54) METHODS AND SYSTEMS FOR PROCESSING BIOMASS MATERIAL

(71) Applicant: SHELL OIL COMPANY, Houston, TX (US)

(72) Inventors: Phillip Guy Hamilon, Sugar Land, TX (US); Corey William Radtke, Katy, TX (US); Keith Michael Kreitman, Houston, TX (US)

(73) Assignee: Shell Oil Company, Houston, TX (US)

( * ) Notice: Subject to any disclaimer, the term of this patent is extended or adjusted under 35 U.S.C. 154(b) by 168 days.

(21) Appl. No.: 13/895,897

(22) Filed: May 16, 2013

(65) Prior Publication Data

US 2013/0305598 A1    Nov. 21, 2013

Related U.S. Application Data

(60) Provisional application No. 61/648,109, filed on May 17, 2012, provisional application No. 61/786,844, filed on Mar. 15, 2013, provisional application No. 61/786,860, filed on Mar. 15, 2013.

(51) Int. Cl.
*C10G 1/00* (2006.01)
*C12P 7/06* (2006.01)
(Continued)

(52) U.S. Cl.
CPC ...... *C10G 1/002* (2013.01); *C10G 1/02* (2013.01); *C10G 3/46* (2013.01); *C10G 3/50* (2013.01);
(Continued)

(58) Field of Classification Search
CPC ............ C10G 1/002; C10G 1/02; C10G 3/46; C10G 3/50; C12P 5/026; C12P 5/02; C12P 5/00; C12P 7/06; C12P 7/00; C12P 7/10; C12F 3/10; Y02E 50/16; Y02E 50/17; Y02T 50/678

See application file for complete search history.

(56) References Cited

U.S. PATENT DOCUMENTS 3,549,319  A   12/1970  Wilson
5,536,325  A    7/1996  Brink
(Continued)

FOREIGN PATENT DOCUMENTS

AU   2013262755   1/2015
AU   2013262757   1/2015
(Continued)

OTHER PUBLICATIONS

Bahree, M., "Sorghum for Ethanol", International United Phosphorous Fuel Sorghum, FORBES Magazine, 2009, pp. 1-6.
(Continued)

*Primary Examiner* — Cephia D Toomer

(57) ABSTRACT

Embodiments of the present invention provide for production and recovery of volatile organic compounds and higher hydrocarbons from biomass material. One embodiment comprises contacting a solid component of a biomass material with a digestive solvent to form a digested biomass stream, and at least a portion of the digested biomass is further thermocatalytically treated to generate higher hydrocarbons. The solid component is generated by a method comprising introducing a biomass material to a compartment of a solventless recovery system, wherein the biomass material contains one or more volatile organic compounds; contacting the biomass material with a superheated vapor stream in the compartment to vaporize at least a portion of an initial liquid content in the biomass material; separating a vapor component and a solid component from the heated biomass material; retaining at least a portion of the gas component for use as part of the superheated vapor stream.

27 Claims, 4 Drawing Sheets

(51) Int. Cl.
| | |
|---|---|
| C12P 7/00 | (2006.01) |
| C12P 5/00 | (2006.01) |
| C12F 3/10 | (2006.01) |
| C10G 3/00 | (2006.01) |
| C12P 7/10 | (2006.01) |
| C12P 5/02 | (2006.01) |
| C10G 1/02 | (2006.01) |

(52) U.S. Cl.
CPC ... *C12F 3/10* (2013.01); *C12P 5/00* (2013.01); *C12P 5/02* (2013.01); *C12P 5/026* (2013.01); *C12P 7/00* (2013.01); *C12P 7/06* (2013.01); *C12P 7/10* (2013.01); *Y02E 50/16* (2013.01); *Y02E 50/17* (2013.01); *Y02T 50/678* (2013.01)

(56) References Cited

U.S. PATENT DOCUMENTS

| | | | |
|---|---|---|---|
| 5,789,210 | A | 8/1998 | Ho et al. |
| 6,475,768 | B1 | 11/2002 | Otero et al. |
| 6,818,803 | B1 | 11/2004 | Austin-Phillips et al. |
| 7,208,530 | B2 * | 4/2007 | Norbeck et al. ............ 518/704 |
| 7,285,179 | B2 | 10/2007 | Snekkenes et al. |
| 7,781,191 | B2 | 8/2010 | Dunson, Jr. et al. |
| 8,480,765 | B2 * | 7/2013 | Siskin et al. .................. 44/605 |
| 8,641,910 | B2 | 2/2014 | Wietgrefe |
| 2003/0162271 | A1 | 8/2003 | Zhang et al. |
| 2008/0216391 | A1 | 9/2008 | Cortright et al. |
| 2009/0239279 | A1 | 9/2009 | Hall et al. |
| 2010/0236988 | A1 | 9/2010 | Gabrielov et al. |
| 2011/0015445 | A1 | 1/2011 | Masuda et al. |
| 2011/0108409 | A1 | 5/2011 | Brown |
| 2011/0154721 | A1 | 6/2011 | Chheda et al. |
| 2011/0154722 | A1 | 6/2011 | Chheda et al. |
| 2011/0282115 | A1 | 11/2011 | Chheda et al. |
| 2012/0317872 | A1 | 12/2012 | Powell et al. |
| 2013/0052709 | A1 | 2/2013 | Wietgrefe et al. |

FOREIGN PATENT DOCUMENTS

| | | |
|---|---|---|
| CA | 2873303 | 11/2013 |
| CN | 101235391 | 8/2001 |
| CN | 101085995 | 12/2007 |
| CN | 101503713 | 8/2009 |
| GB | 2201413 | 9/1988 |
| JP | 2009136201 | 6/2009 |
| JP | 2009136202 | 6/2009 |
| JP | 2011182685 | 9/2011 |
| JP | 2012055302 | 3/2012 |
| WO | 9113099 | 9/1991 |
| WO | 9513362 | 5/1995 |
| WO | 9742307 | 11/1997 |
| WO | 9745430 | 12/1997 |
| WO | 9811235 | 3/1998 |
| WO | 2005093041 | 10/2005 |
| WO | 2006096130 | 9/2006 |
| WO | 2007028811 | 3/2007 |
| WO | 2007100897 | 9/2007 |
| WO | 2007127912 | 11/2007 |
| WO | 2007136762 | 11/2007 |
| WO | 2008119082 | 10/2008 |
| WO | 200958276 | 5/2009 |
| WO | 2009109631 | 9/2009 |
| WO | 2010028206 | 3/2010 |
| WO | 2010065643 | 6/2010 |
| WO | 2010096510 | 8/2010 |
| WO | 2010107944 | 9/2010 |
| WO | 2011039635 | 4/2011 |
| WO | 2011057159 | 5/2011 |
| WO | 2012061596 | 5/2012 |
| WO | 2012145123 | 10/2012 |
| WO | 2013173560 | 11/2013 |
| WO | 2013173562 | 11/2013 |
| WO | 2013173563 | 11/2013 |
| WO | 2013173576 | 11/2013 |

OTHER PUBLICATIONS www.azda.gov, "Agriculture Improving Air Quality", Guide to Agriculture PM10 Best Management Practices, Governor's Agriculture BMP Committee, 2008, pp. 1-29.

Morey, R.V. et al., "Superheated Steam Drying Technology in an Ethanol Production Process", An ASABE Meeting Presentation, Paper No. 1009069, 2010, Pittsburgh, PA, pp. 1-11.

GEA Barr-Rosin, "Superheated Steam Dryer and Processor", Environmental and Energy Saving Drying Technology Treatment of Oil Seeds, Beans and Proteins, Brochure, GEA Group AG.

Brooks, R., et al., "Bioconversion of Plant Biomass to Ethanol", General Electric Corporate Research & Development, NY, pp. 275-280.

Kitamoto, "Production of Bio-Ethanol by Solid State Fermentation of Cellulosic Biomass", Bio R&D, vol. 26, No. 12, (2009) pp. 52-57.

Zhu, J.Y, et al., "Woody Biomass Pretreatment for Cellulosic Ethanol Production: Technology & Energy Consumption Evaluation", Bioresource Technology, vol. 101, (2010) pp. 4992-5002.

Bryan, W., "Solid-State Fermentation of Sugars in Sweet Sorghum"; Enzyme Microb. Technal., 1990, vol. 12, pp. 437-442.

Hendriks, A.T.W.M. et al., Pretreatments to Enhance the Digestibility of Lignocellulosic Biomass, Bioresource Technology, 2009, vol. 100, pp. 10-18.

Needleman, S.B. et al., "A General Method Applicable to the Search for Similarities in the Amino Acid Sequence if Two Proteins", J. Mol. Biol. (1970) vol. 48, pp. 443-453.

International Search Report dated Aug. 19, 2013, for Application No. PCT/US2013/041306 filed May 16, 2013.

Sagehashi, M. et al., "Superheated Steam Pyrolysis of Biomass Elemental Components and Sugi (Japanese cedar) for Fuels and Chemicals", Bioresource Technology, (2006) vol. 97, pp. 1272-1283.

Renon, Henry, et al.; "Local Compositions in Thermodynamic Excess Functions for Liquid Mixtures"; AIChE J.; vol. 14(I), pp. S.135-S.144; 1968.

Gupta, Rajan, et al., Liquid-Liquid Extraction Using the Composition-Induced Phase Separation Process; Ind. Eng. Chem. Res. Vo. 35; pp. 2360-2368; 1996.

Li, N. et al., Renewable gasoline from aqueous phase hydrodeoxygenation of aqueous sugar solutions prepared by hydrolysis of maple wood, The Royal Society of Chemistry Jan. 1, 2011, Green Chemistry, vol. 13, No. 1., pp. 91-101 XP002677263.

Henk, L. et al.; "Solid State Production of Ethanol from Sorghum"; Applied Biochemistry and Biotechnology; vol. 57/58; pp. 489-501; 1996.

Webster, W, et al: "Observations of the Harvesting, Transporting and Trial Crushing of Sweet Sorghum in a Sugar Mill"; 2004 Conference of the Australian Society of Sugar Cane Technologist; Queensland, Australia; 2 pages;; May 2004.

Andrzejewski et al.; "Development of commercially viable processing technologies for sweet sorghum"; USDA-ARS-Southern Regional Research Center; Sweet Sorghum Ethanol Conference; Jan. 26, 2012.

Bellmer, D; "The untapped potential of Sweet Sorghum as a Bioenergy Feedstock"; Sweet Sorghum ethanol Conference; pp. 1-33; Jan. 26, 2012.

Wu et al.; "Features of sweet sorghum juice and their performance in ethanol fermentation"; Industrial Crops and Products; vol. 31; pp. 164-170; 2010.

Bennet et al; "Farm-gate productions costs of sweet sorghum as a bioethanol feedstock"; Transactions of the American Society of Agricultural and Biological Engineers; vol. 5(2); pp. 602-613; 2008.

Shen et al.; "Research on Solid-State Ethanol Fermentation Using Dry Sweet Sorghum Stalk Particles with Active Dry Yeast"; Energy & FUels; vol. 23; pp. 519-525; 2009.

Iman et al.; Ethanol Fermentation from Sweet Sorghum Juice; ASABE Annual International Meeting; Pittsburge, PA; pp. 1-8; Jun. 2010.

(56) References Cited

OTHER PUBLICATIONS

Lingle, et al.; "Post-harvest Changes in Sweet Sorghum I: Brix and Sugars"; Bioenerg. Res.; vol. 5; pp. 158-167; 2012.

Radtke, et al. "Milestone Completion Report"; Idaho National Laboratory; pp. 1-30; Sep. 29, 2007.

Noah, et al.; "Extraction of Ensiled Sweet Sorghum with a Continuous Countercurrent Diffuser"; American Society of Agricultural Engineers; vol. 32, No. 4; pp. 1419-1425; Jul.-Aug. 1989.

Schmidt, et al.; "Preservation of Sugar Content in Ensiled Sweet Sorghum"; Bioresource Technology; vol. 60; pp. 9-13; 1997.

Bellmer, et al. "The untapped potential of sweet sorghum as a bioenergy feedstock"; Biofuels, vol. 1(4); pp. 563-573; 2010.

Radtke, et al., Crossover 2007 Bioenergy: From Fields to Wheels Presentation; pp. 1-22; Sep. 4, 2007.

Morgan et al; Volatile constituents of grass and corn silage.I. Steam distillates; Journal of Dairy Science; vol. 45, No. 4; pp. 457-466; Apr. 22, 2001.

International Search Report for PCT/US2013/041309 dated Sep. 5, 2013; 5 pages.

International Search Report for PCT/US2013/041313 dated Sep. 2, 2013; 5 pages.

Bahrin, E. K. et al., "Physicochemical Property Changes and Enzymatic Hydrolysis Enhancement of Oil Palm Empty Fruit Bunches Treated with Superheated Steam", Bioresources, 2012, vol. 7(2), pp. 1784-1801.

Kosaric, N. et al., "Ethanol", Ullmanns Encyclopedia of Industrial Chemistry, 2011, vol. 13, pp. 333-403.

Morey, R. V., "Biomass Electricity Generation at Ethanol Plants-Achieving Maxiumum Impact", University of Minnesota, 2009, pp. 1-20, xcelenergy.com.

\* cited by examiner

METHODS AND SYSTEMS FOR PROCESSING BIOMASS MATERIAL

CROSS-REFERENCE TO RELATED APPLICATIONS

The present application claims priority to U.S. Provisional Application No. 61/648,109, filed on May 17, 2012, U.S. Provisional Application No. 61/786,844, filed on Mar. 15, 2013, and U.S. Provisional Application No. 61/786,860, filed on Mar. 15, 2013, the disclosures of which are incorporated by reference herein in their entirety.

FIELD OF THE INVENTION

Embodiments of this invention relate generally to a process for the manufacture of volatile organic compounds and hydrocarbons from biomass material and more particularly to manufacturing and recovery of volatile organic compounds through fermentation of biomass material and manufacturing of hydrocarbons using a product therefrom.

BACKGROUND

This section is intended to introduce various aspects of the art, which may be associated with exemplary embodiments of the present invention. This discussion is believed to assist in providing a framework to facilitate a better understanding of particular aspects of the present invention. Accordingly, it should be understood that this section should be read in this light, and not necessarily as admissions of any prior art.

As the world's petroleum supplies continue to diminish there is a growing need for alternative materials that can be substituted for various petroleum products, particularly transportation fuels. A significant amount of effort has been placed on developing new methods and systems for providing energy from resources other than fossil fuels. Currently, much effort is underway to produce bioethanol and biofuels from renewable biomass materials. One type of biomass is plant biomass, which contains a high amount of carbohydrates including sugars, starches, celluloses, lignocelluloses, hemicelluloses. Efforts have particularly been focused on ethanol from fermentable sugar and hydrocarbons from cellulosic materials.

Conventional ethanol production from corn typically competes with valuable food resources, which can be further amplified by increasingly more severe climate conditions, such as droughts and floods, which negatively impact the amount of crop harvested every year. The competition from conventional ethanol production can drive up food prices. While other crops have served as the biomass material for ethanol production, they usually are not suitable for global implementations due to the climate requirements of such crops. For instance, ethanol can also be efficiently produced from sugar cane, but only in certain areas of the world, such as Brazil, that have a climate that can support near-year-round harvest. Current processes aiming to convert carbohydrates to higher hydrocarbons are limited to feedstock that includes unprocessed biomass materials or municipal solid waste (MSW). Unprocessed biomass includes sugarcane bagasse, forest resources, crop residues, and wet/dry harvested energy crops. These conventional feedstock sources require storage, transportation, particle size reduction, and additional front end processing before they can be introduced into the conversion process to hydrocarbon. For example, baling of biomass is costly and can result in hazards such as fire, rodent, dust, unwanted debris (such as rocks) and hantavirus. Further, bales and forest resources are more costly to transport than denser material and more costly to handle than materials that are already particle size reduced and do not need to be further formatted. MSW further has challenges related to contamination with regulated hazardous metals that can contribute to risks of poor fuel quality as well as health and safety risks. Forest resources, such as trees, are cumbersome to transport. Further, forest resources require debarking, chopping to wood chips of desirable thickness, and washing to remove any residual soil, dirt and the like. Therefore, there is still a need for a biomass that addresses these challenges.

SUMMARY

Embodiments of the invention can address the challenges mentioned above as well as provide other advantages and features. In one embodiment, the feedstock can come from the solid component exiting a volatile organic compound recovery system. In that embodiment, the feedstock is entrained in an engineered system where it is already flowing and preformatted, which allows the feedstock to be routed directly into the reaction for conversion to hydrocarbons and other chemicals as desired. Embodiments of the invention can provide for a volatile organic compound recovery equipment and biomass to hydrocarbon production equipment to be located near each other. Such embodiments can allow for production of volatile organic compounds, hydrocarbons, and other chemicals from one facility, which reduces storage, handling, transportation and feedstock preparation costs associated with other feedstock before it can enter the production flow of the conversion process from biomass to hydrocarbons and other chemicals. Such embodiments can also provide a continuous supply of feedstock that is already particle size reduced in contrast to conventional feedstock that often requires storage, transportation, and/or size reduction at or prior to arriving at the plant for processing to hydrocarbons, which reduces the particular associated costs.

The feedstock of certain embodiments can also have lower handling and transportation costs when it is transported to other locations for processing into hydrocarbons and other materials. Unlike other conventional feedstock sources, such as forest resources, the feedstock of certain embodiments exits the volatile organic compound recovery system in a preformatted manner that is already particle-size reduced, which can reduce or eliminate the front end processing costs before the feedstock can enter the conversion process to hydrocarbon and other chemicals. The preformatted size distribution of the feedstock of certain embodiments of the invention places it in a denser form than other conventional feedstock sources, which can reduce transportation cost as more of the feedstock of these embodiments can be transported per volume. Embodiments of the invention can provide a supply of feedstock that is available year-round independent of a harvest period particular to a biomass material and does not compete with valuable food sources for human.

In one embodiment, a biomass material is prepared to generate volatile organic compounds. The volatile organic compounds are recovered from the prepared biomass material by introducing the prepared biomass material to a compartment of a solventless recovery system; contacting the biomass material with a superheated vapor stream in the compartment to vaporize at least a portion of an initial liquid content in the prepared biomass material, the superheated vapor stream comprising at least one volatile organic compound; separating a vapor component and a solid component from the heated biomass material, where the vapor component comprises at least one volatile organic compound; and retaining at least a portion of the gas component for use as part of the superheated vapor stream. At least a portion of the solid component is further processed to generate hydrocarbons and/or other chemicals. In one embodiment, the further processing comprises contacting the solid component feedstock with a digestive solvent to form a digested biomass stream comprising carbohydrates; contacting the digested biomass stream with molecular hydrogen in the presence of a molecular hydrogen activating catalyst to form a hydrocatalytically treated mixture comprising a plurality of oxygenated hydrocarbon molecules. At least a first portion of the hydrocatalytically treated mixture is recycled to form at least part of the digestive solvent. At least a second portion of the hydrocatalytically treated mixture is processed to form a plurality of higher hydrocarbons. In one embodiment, the higher hydrocarbons are used to form a fuel blend.

In another embodiment, the digestive solvent comprises an organic solvent having partial miscibility with water at 25 degrees C. and the organic solvent to water mass ratio in the digested biomass stream is greater than 1:1. For embodiments using an organic solvent, the hydrocatalytically treated mixture is phase separated by liquid-liquid separation into an organic hydrocarbon-rich phase and a water phase. At least a portion of the organic hydrocarbon-rich phase is recycled as at least part of the organic solvent. At least a portion of the water phase and/or the organic hydrocarbon-rich phase is processed to form higher hydrocarbons.

In one embodiment, the prepared biomass is generated by adding to the biomass at least one additive added, wherein said at least one additive comprise a microbe, and optionally, an acid and/or an enzyme; and storing the prepared biomass material for at least about 24 hours in a storage facility to allow for the production of at least one volatile organic compound from at least a portion of the sugar.

In addition to the features described above, embodiments of the invention allow for economical production of alternative fuels, such as ethanol, other volatile organic compounds, hydrocarbons, and other chemicals, from plants that contain fermentable sugar by addressing challenges, such as costs of storage and transportation, short harvest windows, quick degradation of sugars, and large investment in equipment. Aspects of the embodiments described herein are applicable to any biomass material, such as plants containing fermentable sugars. The features of embodiments of the present invention allow for economical use of various plants to produce alternative fuels and chemicals and are not limited to sorghum and other plants that suffer similar challenges. Such challenging crops are highlighted herein because other methods and systems have not been able to economically use these challenging crops to produce fuels and chemicals. As such, the specific mention of sorghum is not intended to be limiting, but rather illustrates one particular application of embodiments of the invention.

Embodiments of the invention allow for the recovery facility to run continuously year-round in a controlled manner independent of the harvest window, thereby broadening the geological locations available to place a recovery facility and/or a conversion to hydrocarbon facility, including areas with a relatively short harvest window.

Other advantages and features of embodiments of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

These drawings illustrate certain aspects of some of the embodiments of the invention, and should not be used to limit or define the invention.

DETAILED DESCRIPTION OF PREFERRED EMBODIMENTS

Figure 1:
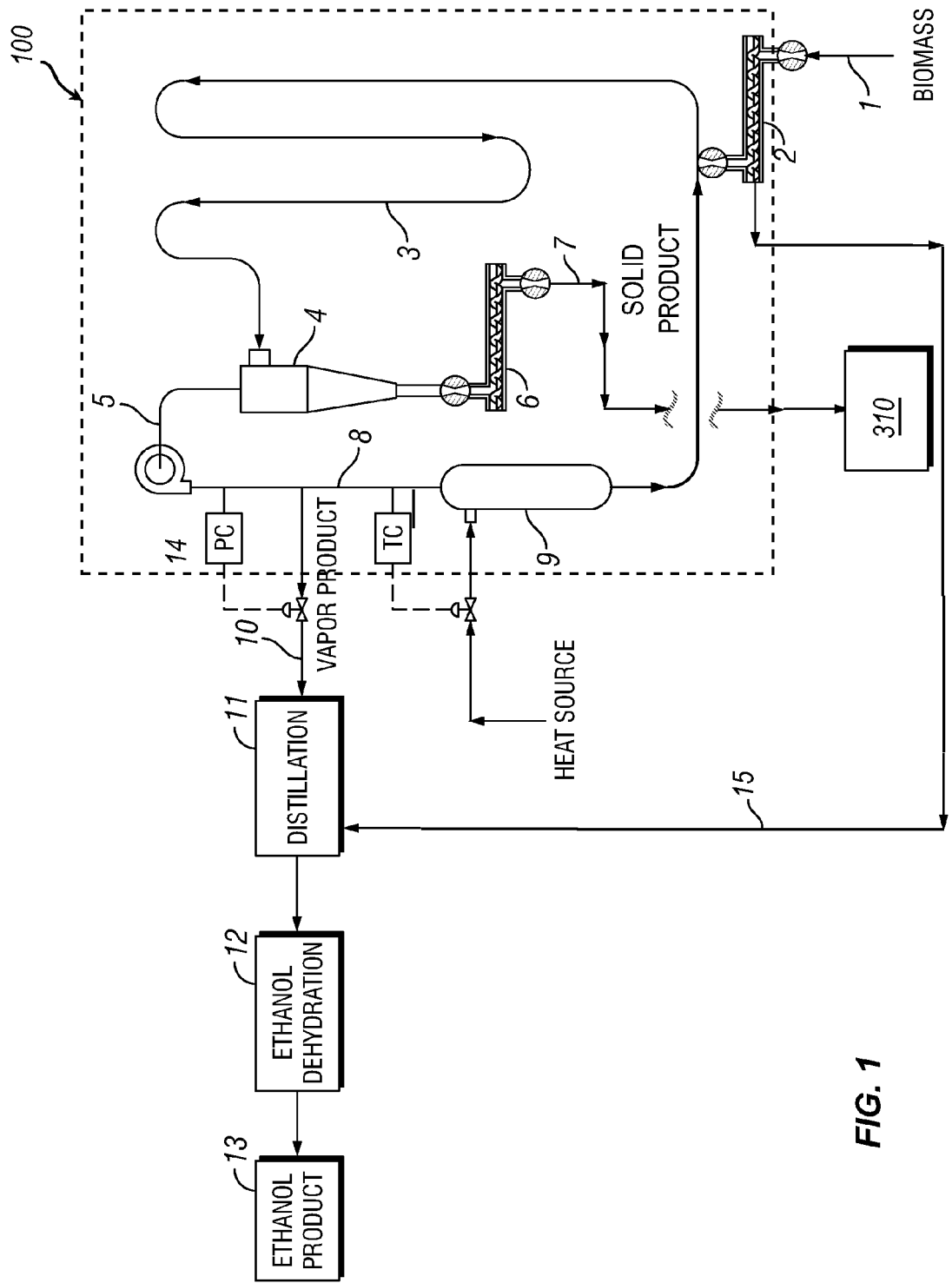
FIG. 1 is a diagram of one embodiment to process biomass material according to certain aspects of the present invention.

Embodiments of the present invention can provide efficient and economical production and recovery of ethanol or other volatile organic compounds, such as acetic acid, from solid biomass material, as well as a feedstock for processing to convert carbohydrate to hydrocarbons. According to one aspect of the invention, a biomass material is prepared to generate volatile organic compounds. The volatile organic compounds are recovered from the prepared biomass material by introducing the prepared biomass material to a compartment of a solventless recovery system; contacting the biomass material with a superheated vapor stream in the compartment to vaporize at least a portion of an initial liquid content in the prepared biomass material, the superheated vapor stream comprising at least one volatile organic compound; separating a vapor component and a solid component from the heated biomass material, where the vapor component comprises at least one volatile organic compound; and retaining at least a portion of the gas component for use as part of the superheated vapor stream. At least a portion of the solid component is further processed to generate hydrocarbons and/or other chemicals. In one embodiment, the further processing comprises contacting the solid component feedstock with a digestive solvent to form a digested biomass stream comprising carbohydrates; contacting the digested biomass stream with molecular hydrogen in the presence of a molecular hydrogen activating catalyst to form a hydrocatalytically treated mixture comprising a plurality of oxygenated hydrocarbon molecules. At least a first portion of the hydrocatalytically treated mixture is recycled to form at least part of the digestive solvent. At least a second portion of the hydrocatalytically treated mixture is processed to form a plurality of higher hydrocarbons. In one embodiment, the higher hydrocarbons are used to form a fuel blend.

In another embodiment, the digestive solvent comprises an organic solvent having partial miscibility with water at 25 degrees C. and the organic solvent to water mass ratio in the digested biomass stream is greater than 1:1. For embodiments using an organic solvent, the hydrocatalytically treated mixture is phase separated by liquid-liquid separation into an organic hydrocarbon-rich phase and a water phase. At least a portion of the organic hydrocarbon-rich phase is recycled as at least part of the organic solvent. At least a portion of the water phase and/or the organic hydrocarbon-rich phase is processed to form higher hydrocarbons.

Biomass Preparation

As used herein, the term "solid biomass" or "biomass" refers at least to biological matter from living, or recently living organisms. Solid biomass includes plant or animal matter that can be converted into fibers or other industrial chemicals, including biofuels. Solid biomass can be derived from numerous types of plants or trees, including miscanthus, switchgrass, hemp, corn, tropical poplar, willow, sorghum, sugarcane, sugar beet, and any energy cane, and a variety of tree species, ranging from eucalyptus to oil palm (palm oil). In one embodiment, the solid biomass comprises at least one fermentable sugar-producing plant. The solid biomass can comprise two or more different plant types, including fermentable sugar-producing plant. In a preferred embodiment not intended to limit the scope of the invention, sorghum is selected, due to its high-yield on less productive lands and high sugar content.

The term "fermentable sugar" refers to oligosaccharides and monosaccharides that can be used as a carbon source (e.g., pentoses and hexoses) by a microorganism to produce an organic product such as alcohols, organic acids, esters, and aldehydes, under anaerobic and/or aerobic conditions. Such production of an organic product can be referred to generally as fermentation. The at least one fermentable sugar-producing plant contains fermentable sugars dissolved in the water phase of the plant material at one point in time during its growth cycle. Non-limiting examples of fermentable sugar-producing plants include sorghum, sugarcane, sugar beet, and energy cane. In particular, sugarcane, energy cane, and sorghum typically contain from about 5% to about 25% soluble sugar w/w in the water phase and have moisture content between about 60% and about 80% on a wet basis when they are near or at their maximum potential fermentable sugar production (e.g., maximum fermentable sugar concentration).

The term "wet basis" refers at least to the mass percentage that includes water as part of the mass. In a preferred embodiment, the sugar producing plant is sorghum. Any species or variety of the genus sorghum that provides for the microbial conversion of carbohydrates to volatile organic compounds (VOCs) can be used. For embodiments using sorghum, the plant provides certain benefits, including being water-efficient, as well as drought and heat-tolerant. These properties make the crop suitable for many locations, including various regions across the earth, such as China, Africa, Australia, and in the US, such as portions of the High Plains, the West, and across the South. Texas.

In embodiments using sorghum, the sorghum can include any variety or combination of varieties that may be harvested with higher concentrations of fermentable sugar. Certain varieties of sorghum with preferred properties are sometimes referred to as "sweet sorghum." The sorghum can include a variety that may or may not contain enough moisture to support the juicing process in a sugar cane mill operation. In a preferred embodiment, the solid biomass includes a Sugar T sorghum variety commercially produced by Advanta and/or a male parent of Sugar T, which is also a commercially available product of Advanta. In a preferred embodiment, the crop used has from about 5 to about 25 brix, preferably from about 10 to about 20 brix, and more preferably from about 12 to about 18 brix. The term "brix" herein refers at least to the content of glucose, fructose, and sucrose in an aqueous solution where one degree brix is 1 gram of glucose, fructose, and/or sucrose in 100 grams of solution and represents the strength of the solution as percentage by weight (% w/w). In another preferred embodiment, the moisture content of the crop used is from about 50% to 80%, preferably at least 60%.

In one embodiment, the crop is a male parent of Sugar T with a brix value of about 18 and a moisture content of about 67%. In another embodiment, the crop is Sugar T with a brix value of about 12 at a moisture content of about 73%. In these particular embodiments, the brix and moisture content values were determined by handheld refractometer.

After at least one additive (a microbe, optionally, an acid and/or enzyme) is added to the solid biomass, it becomes prepared biomass material where the at least one additive facilitates the conversion of fermentable sugar into a VOC (such as ethanol). As noted above and further described below, the prepared biomass material can be stored for a certain period of time to allow more VOCs to be generated by the conversion process. At least one volatile organic compound is then recovered from the prepared biomass material. Volatile organic compounds are known to those skilled in the art. The U.S. EPA provides descriptions volatile organic compounds (VOC), one of which is any compound of carbon, excluding carbon monoxide, carbon dioxide, carbonic acid, metallic carbides or carbonates, and ammonium carbonate, which participates in atmospheric photochemical reactions, except those designated by EPA as having negligible photochemical reactivity (see http://www.epa.gov/iaq/voc2.html#definition). Another description of volatile organic compounds, or VOCs, is any organic chemical compound whose composition makes it possible for them to evaporate under normal indoor atmospheric conditions of temperature and pressure. This is the general definition of VOCs that is used in the scientific literature, and is consistent with the definition used for indoor air quality. Normal indoor atmospheric conditions of temperature and pressure refer to the range of conditions usually found in buildings occupied by people, and thus can vary depending on the type of building and its geographic location. One exemplary normal indoor atmospheric condition is provided by the International Union of Pure and Applied Chemistry (IUPAC) and the National Institute of Standards and Technology (NIST). IUPAC's standard is a temperature of 0° C. (273, 15 K, 32° F.) and an absolute pressure of 100 kPa (14.504 psi), and NIST's definition is a temperature of 20° C. (293, 15 K, 68° F.) and an absolute pressure of 101.325 kPa (14.696 psi).

Since the volatility of a compound is generally higher the lower its boiling point temperature, the volatility of organic compounds are sometimes defined and classified by their boiling points. Accordingly, a VOC can be described by its boiling point. A VOC is any organic compound having a boiling point range of about 50 degrees C. to 260 degrees C. measured at a standard atmospheric pressure of about 101.3 kPa. Many volatile organic compounds that can be recovered and/or further processed from VOCs recovered from embodiments of the present invention have applications in the perfume and flavoring industries. Examples of such compounds may be esters, ketones, alcohols, aldehydes, hydrocarbons and terpenes. The following Table 1 further provides non-limiting examples of volatile organic compounds that may be recovered and/or further processed from VOCs recovered from the prepared biomass material.

TABLE 1

| Methanol | Ethyl acetate | Acetaldehyde | Diacetyl |
|---|---|---|---|
| 2,3-pentanedione | Malic acid | Pyruvic acid | Succinic acid |
| Butyric acid | Formic acid | Acetic acid | Propionic acid |
| Isobutyric acid | Valeric acid | Isovaleric acid | 2-methylbutyric acid |
| Hexanoic acid | Heptanoic acid | Octanoic acid | Nonanoic acid |
| Decanoic acid | Propanol | Isopropanol | Butanol |
| Isobutanol | Isoamyl alcohol | Hexanol | Tyrosol |
| Tryptoptanol | Phenethyl alcohol | 2,3-butanediol | Glycerol |
| Fumaric acid | Ethanol | Amyl alcohol | 1,2-propanol |
| 1-propanol | 2-butanol | Methyl acetate | Ethyl acetate |

TABLE 1-continued

| Propyl acetate | Ethyl lactate | Propyl lactate | Acetone |
| --- | --- | --- | --- |
| Ethyl formate | n-propyl alcohol | 2-methyl-1-propanol | 2-propen-1-ol |
| | 3-buten-2-ol | | |
| 2,3-methyl-1-butanol | | | |

Ethanol is a preferred volatile organic compound. As such, many examples specifically mention ethanol. This specific mention, however, is not intended to limit the invention. It should be understood that aspects of the invention also equally apply to other volatile organic compounds. Another preferred volatile organic compound is acetic acid.

Embodiments of the present invention provide for the long term storage of solid biomass material without significant degradation to the volatile organic compounds contained in the prepared biomass material, and they provide for sugar preservation to allow for continued generation of VOCs. As used in this context, "significant" refers at least to within the margin of error when measuring the amount or concentration of the volatile organic compounds in the prepared biomass material. In one embodiment, the margin of error is about 0.5%.

Accordingly, embodiments of the present invention allow for continuous production VOCs without dependence on the length of the harvest, thereby eliminating or minimizing down time of a recovery plant in traditional just-in-time harvest and recovery processes. As such, embodiments of the present invention allow for harvest of the crop at its peak without compromises typically made to lengthen the harvest season, such as harvest slightly earlier and later than peak time. That is, embodiments of the invention allow for harvest at high field yields and high sugar concentrations, such as when the selected crop has reached its peak sugar concentration or amount of fermentable sugars that can be converted into a volatile organic compound, even if this results in a shorter harvest period. In one embodiment, the solid biomass is harvested or prepared when it is at about 80%, about 85%, about 90%, about 95%, or about 100% of its maximum potential fermentable sugar concentration. As such, embodiments of the present invention, particularly the recovery phase, can be operated continuously year-round without time pressure from fear of spoilage of the solid biomass and VOCs contained therein. While embodiments of the present invention allow for harvest of the solid biomass near or at its maximum sugar production potential, the solid biomass material can be harvested at any point when it is deemed to contain a suitable amount of sugar. Further, the harvest window varies depending on the type of crop and the geographical location. For example, the harvest window for sorghum in North America can range from about 1 to 7 months. However, in Brazil and other equatorial and near equatorial areas, the harvest window may be up to twelve months.

In embodiments using plants as the solid biomass, the solid biomass can be collected or harvested from the field using any suitable means known to those skilled in the art. In one embodiment, the solid biomass comprises a stalk component and a leaf component of the plant. In another embodiment, the solid biomass further comprises a grain component. In a preferred embodiment, the solid biomass is harvested with a forage or silage harvester (a forage or silage chopper). A silage or forage harvester refers to farm equipment used to make silage, which is grass, corn or other plant that has been chopped into small pieces, and compacted together in a storage silo, silage bunker, or in silage bags. A silage or forage harvester has a cutting mechanism, such as either a drum (cutterhead) or a flywheel with a number of knives fixed to it, which chops and transfers the chopped material into a receptacle that is either connected to the harvester or to another vehicle driving alongside. A forage harvester is preferred because it provides benefits over a sugar cane harvester or dry baled system. For example, a forage harvester provides higher density material than a sugar cane harvester, thereby allowing for more efficient transportation of the harvested material. In one embodiment, using a forage harvester results in harvested sorghum with a bulk density of about 400 kg/m$^3$, compared to sugarcane harvested with a sugarcane harvester with density of about 300 kg/m$^3$, and for sorghum harvested with a sugarcane harvester with a density of about 200 kg/m$^3$. In general, higher bulk density material is cheaper to transport, which tends to limit the geographical area in which cane-harvested crop can be sourced.

Thus, a forage harvester is an overall less expensive way to harvest the selected biomass, such as sorghum, than a cane harvester or dry baled system. Not to be bound by theory, it is believed the cost savings are due in part to higher material throughputs and the higher bulk density of the solid biomass harvested by a forage harvester. The solid biomass can be cut in any length. In one embodiment, the chop lengths of the harvester can be set to a range of about 3 mm to about 80 mm, preferably about 3 mm to about 20 mm, with examples of about 3 mm to about 13 mm chop lengths being most preferred. At these preferred chop lengths, there was not observable aqueous discharge in the forage harvester, so losses were minimal. When a chop length is selected, the harvester provides biomass with an average size or length distribution of about the chop length selected. In one embodiment, the average size distribution of the solid component exiting the recovery system can be adjusted as desired, which can be done by adjusting the chop length of the harvester.

At least one additive is added to the solid biomass to facilitate and/or expedite the conversion of appropriate carbohydrates into volatile organic compounds. After selected additive(s) have been added, the solid biomass can be referred to as prepared biomass material. In one embodiment, the prepared biomass material can comprise at least one or any combination of fermentable sugar-producing plants listed above. In a preferred embodiment, the selected additive(s) can be conveniently added using the harvester during harvest.

In one embodiment, at least about 700 tons, preferably at least about 1 million tons, such as at least 1.2 million tons, or more preferably about at least 5 million tons of prepared biomass material is generated in a particular harvest window based on the growing conditions of a specific region, such as about 1 to 7 months in North America for sorghum.

The at least one additive can be added at any point during and/or after the harvest process. In a preferred embodiment using a forage harvester, additives are added to the solid biomass during the harvest process to generate a prepared biomass material. In particular, forage harvesters are designed for efficiently adding both solid and liquid additives during harvest. As mentioned above, the additives added include at least a microbe (e.g. a yeast), and optionally, an acid and/or an enzyme. In a preferred embodiment, the selected additive(s) are added as solutions. Additional details of the potential additives are further provided below.

For embodiments using a forage harvester or a similar equipment, the selected additive(s) can be added during harvest at all phases, such as before the intake feed rollers, during intake, at chopping, after chopping, through the blower, after the blower, in the accelerator, in the boom (or spout), and/or after the boom. In one embodiment where acid and enzyme are added, the acid is added near the intake feed rollers, and a microbe and the enzyme are added in the boom. In a particular embodiment, a Krone Big X forage harvester with a V12 motor with an about 30 ft wide header is used. In an embodiment using the Krone system, the acid is added as a solution through flexible tubing that discharged the solution just in front of the feed rollers. In this way, the liquid flow can be visually monitored, which showed the acid solution and solid biomass quickly mixed inside the chopping chamber. In another embodiment, the addition of acid was also demonstrated as a viable practice using a Case New Holland FX 58 forage harvester. In certain embodiments, the forage harvester used can include an onboard rack for containing additives, at least the one(s) selected to be added during harvest. In another embodiment, the selected additive(s) to be added during harvest may be towed behind the harvester on a trailer. For example, in one embodiment, it was demonstrated that a modified utility trailer equipped with tanks containing additive solutions of yeast, enzymes and acid can be employed with minimal interfering with normal operations of the harvester, thereby substantially maintaining the expected cost and duration of the harvest process. For example, a normal harvest configuration and biomass yield employing a silage harvester travelling at about 4 miles per hour maintains a similar rate of collection of about 4 miles per hour when equipped with certain additives as described above in one embodiment.

In embodiments of the present invention, the prepared biomass material is eventually transported to a storage facility where it is stored for a period of time to allow for production of at least one volatile organic compound from at least a portion of the fermentable sugar of the solid biomass. The details of the storage phase are further provided below. In certain embodiments, selected additive(s) can also be added at the storage facility. For example, in one embodiment, the selected additive(s) can be added during unloading or after the solid biomass has been unloaded at the storage facility. In one embodiment, a conveyance system is used to assist with the adding of selected additive(s) at the storage facility. Additive(s) added at the storage facility to solid biomass can be one(s) that have not been added or additional amount of one(s) previously added. Accordingly, selected additive(s) can therefore be added at any point from the start of the harvest process to prior to storage of the prepared biomass material at the storage area or facility, such as at points where the material is transferred.

As mentioned above, additive(s) for embodiments of the present invention include at least a microbe and optionally, an acid and/or an enzyme. Selected additive(s) can be added to the solid biomass in any order. In a preferred embodiment, an acid is added to the solid biomass before adding a microbe to prime the material to provide an attractive growth environment for the microbe.

In a preferred embodiment, acid is added to reduce the pH of the solid biomass to a range that facilitates and/or expedites selected indigenous or added microbial growth, which increases production of ethanol and/or volatile organic compounds. The acid can also stop or slow plant respiration, which consumes fermentable sugars intended for subsequent VOC production. In one embodiment, acid is added until the pH of the solid biomass is between about 2.5 and about 5.0, preferably in a range of about 3.7 to about 4.3, and more preferably about 4.2. The acid used can include known acids, such as sulfuric acid, formic acid, or phosphoric acid. The following Table 2 provides non-limiting examples of an acid that can be used individually or in combination.

TABLE 2

| Sulfuric Acid | Formic Acid | Propionic Acid | Malic Acid |
|---|---|---|---|
| Phosphoric Acid | Maleic Acid | Folic Acid | Citric Acid |

In a preferred embodiment, after the solid biomass has reached the desired pH with the addition of acid, a microbe is added. A microbe in the additive context refers at least to a living organism added to the solid biomass that is capable of impacting or affecting the prepared biomass material. One exemplary impact or effect from added microbe(s) includes providing fermentation or other metabolism to convert fermentable sugars from various sources, including cellulosic material, into ethanol or other volatile organic compounds. Another exemplary impact or effect may be production of certain enzyme(s) that help to deconstruct cellulose in the prepared biomass material into fermentable sugars which can be metabolized to ethanol or other VOC. Yet another exemplary impact or effect provided by a microbe includes production of compounds such as vitamins, co-factors, and proteins that can improve the quality, and thus value, of an eventual by-product that can serve as feed for animals. Further, microbial activity provides heat for the pile. Parts of the microbial cell walls or other catabolite or anabolite may also offer value-added chemicals that may be recovered by a recovery unit. These impacts and effects may also be provided by microbes indigenous to the solid biomass.

Any microbe that is capable of impacting or affecting the prepared biomass material can be added. In a preferred embodiment, the microbe(s) can include microbes used in the silage, animal feed, wine, and industrial ethanol fermentation applications. In one embodiment, the microbe selected includes yeast, fungi, and bacteria according to application and the desired profile of the organic molecule to be made. In a preferred embodiment, yeast is the selected microbe. In another embodiment, bacteria can be added to make lactic acid or acetic acid. Certain fungi can also be added to make these acids. For example, *Acetobacterium acetii* can be added to generate acetic acid; *Lactobacillus, Streptococcus thermophilus* can be added to generate lactic acid; *Actinobacillus succinogenes, Mannheimia succiniciproducens*, and/or *Anaerobiospirillum succiniciproducens* can be added to generate succinic acid; *Clostridium acetobutylicum* can be added to generate acetone and butanol; and/or *Aerobacter aerogenes* can be added to generate butanediol.

The following Table 3 provides non-limiting examples of preferred microbes, which can be used individually or in combination.

TABLE 3

| *Saccharomyces cerevisiae* | *Saccharomyces japonicas* | *Saccharomyces bayanus* | *Saccharomyces fermentatti* |
|---|---|---|---|
| *Saccharomyces exiguous* | *Saccharomyces chevalieri* | *Clostridium acetobutylicum* | *Clostridium amylosaccharobutyl propylicum* |
| *Clostridium* propyl-butylicum | *Clostridium viscifaciens* | *Clostridium propionicum* | *Aerobacter* species |

TABLE 3-continued

| Aerobacter aerogenes | Zymomonas mobilis | Zymomonas species | Clostridium species |
|---|---|---|---|
| Saccharomyces species | Bacillus species | Clostridium thermocellum | Lactobacillus buchneri |
| Lactobacillus plantarum | Enterococcus faecium | Pediococcus species | Propionibacteria |
| Acetobacterium acetii | Streptococcus thermophilus | Lactobacillus paracasei | Lactobacillus species |
| Actinobacillus succinogenes | Mannheimia succiniciproducens | Anaerobiospirillum succiniciproducens | |

Preferred microbes also include *Saccharomyces cerevisiae* strains that can tolerate high ethanol concentrations and are strong competitors in its respective microbial community. The microbes may be mesophiles or thermophiles. Thermophiles are organisms that grow best at temperatures above about 45° C., and are found in all three domains of life: Bacteria, Archaea and Eukarya. Mesophiles generally are active between about 20° C. and 45° C. In an embodiment using a strain of *Saccharomyces cerevisiae*, the strain can come from a commercially available source such as Biosaf from Lesaffre, Ethanol Red from Phibro, and Lallamand activated liquid yeast. If the microbe is obtained from a commercial source, the microbe can be added according to the recommended rate of the provider, which is typically based on the expected sugar content per wet ton, where water is included in the mass calculation. The term "wet ton" refers at least to the mass unit including water. The recommended amount can be adjusted according to reaction conditions. The microbe added can comprise one strain or multiple strains of a particular microbe. In one embodiment, the microbes are added at a rate of up to 500 mL per wet ton of solid biomass. In a particular embodiment using commercially available yeast, about 300 mL of Lallamand yeast preparation is added per wet ton of solid biomass. In another embodiment, an additional yeast strain can be added. For example, Ethanol Red can be added at a rate between about 0.001 kg/wet ton to about 0.5 kg/wet ton, particularly about 0.1 kg/wet ton. In yet another embodiment, another yeast strain can be added, e.g., Biosaf, at a rate between about 0.001 kg/wet tone to about 0.5 kg/wet ton, particularly about 0.1 kg/wet ton. It is understood that other amounts of any yeast strain can be added. For example, about 10%, about 20%, about 30%, about 40%, about 50%, about 60%, about 70%, about 80%, about 90%, about 1.5 times, about 2 times, about 2.5 times, or about 3 times of the provided amounts of microbes can be added.

In certain embodiments, an enzyme is further added. The enzyme can be one that assists in the generation of fermentable sugars from plant materials that are more difficult for the microbe to metabolize, such as different cellulosic materials, and/or to improve the value of an eventual by-product serving as animal feed, such as by making the feed more digestable. The enzyme can also be an antibiotic, such as a lysozyme as discussed further below. The enzyme added can include one type of enzyme or many types of enzymes. The enzyme can come from commercially available enzyme preparations. Non-limiting examples of enzymes that assist in converting certain difficult to metabolize plant materials into fermentable sugars include cellulases, hemicellulases, ferulic acid esterases, and/or proteases. Additional examples also include other enzymes that either provide or assist the provision for the production of fermentable sugars from the feedstock, or increase the value of the eventual feed by-product.

In certain embodiments, the enzymes that assist in converting certain difficult to metabolize plant materials into fermentable sugars can be produced by the plant itself, e.g. in-plantae. Examples of plants that can produce cellulases, hemicellulases, and other plant-polymer degrading enzymes may be produced within the growing plants are described in the patent publications and patent WO2011057159, WO2007100897, WO9811235, and U.S. Pat. No. 6,818,803, which show that enzymes for depolymerizing plant cell walls may be produced in plants. In another embodiment, ensilagement can be used to activate such plant produced enzymes as well as temper the biomass for further processing. One example is described in patent publication WO201096510. If used, such transgenic plants can be included in the harvest in any amount. For example, certain embodiments may employ in-plantae enzymes produced in plants by using particular transgenic plants exclusively as a feedstock, or incorporating the transgenic plants in an interspersed manner within like or different crops.

In certain embodiments that include such plant-polymer degrading enzymes, ethanol can be produced from cellulosic fractions of the plant. In a particular embodiment, when Novazymes CTEC2 enzyme was added to a sorghum storage system in excess of the recommended amount, about 100 times more than the recommended amount, about 152% of the theoretical ethanol conversion efficiency based on the initial free sugar content was achieved. While such an amount of enzymes can be added using commercially available formulations, doing so can be costly. On the other hand, such an amount of enzymes can be obtained in a more cost effective manner by growing transgenic plants that produce these enzymes at least interspersingly among the biomass crop.

The ethanol production from cellulose occurred during the storage phase, e.g., in silage and was stable for about 102 days of storage, after which the experiment was terminated. This demonstrates that, under the conditions of that particular experiment, an excess of such enzyme activity results in at least about 52% production of ethanol using fermentable sugars from cellulose. Not intended to be bound by theory, for certain embodiments, the immediate addition of acid during harvest in the experiment may have lowered the pH, thereby potentially inducing the enzyme activity, which otherwise could damage the plants if produced while the plants were still growing.

In a preferred embodiment, if an enzyme is added, the enzyme can be any family of cellulase preparations. In one embodiment, the cellulose preparation used is Novozymes Cellic CTec 2 or CTec 3. In another embodiment, a fibrolytic enzyme preparation is used, particularly, Liquicell 2500. If used, the amount of enzyme added to degrade plant polymer can be any amount that achieves the desired conversion of plant material to fermentable sugar, such as the recommended amount. In a particular embodiment, about 80,000 FPU to about 90,000,000 FPU, preferably about 400,000 FPU to about 45,000,000 FPU, more preferably about 800,000 FPU to about 10,000,000 FPU of enzyme is added per wet ton of biomass. The term "FPU" refers to Filter Paper Unit, which refers at least to the amount of enzyme required to liberate 2 mg of reducing sugar (e.g., glucose) from a 50 mg piece of Whatman No. 1 filter paper in 1 hour at 50° C. at approximately pH 4.8.

In certain other embodiments, selected additive(s) added can include other substances capable of slowing or controlling bacterial growth. Non-limiting examples of these other substances include antibiotics (including antibiotic enzymes), such as Lysovin (lysozyme) and Lactrol® (Virginiamycin, a bacterial inhibitor). Control of bacterial growth can allow the appropriate microbe to expedite and/or provide the production of volatile organic compounds. Antibiotic is a general term for something which suppresses or kills life. An example of an antibiotic is a bacterial inhibitor. In one embodiment, a selective antibiotic that is intended to impact bacteria and not other microbes is used. One example of a selective antibiotic is Lactrol, which affects bacteria but does not affect yeasts.

In a particular embodiment, if used, Lactrol can be added at rates of about 1 to 20 part-per-million (ppm) w/v (weight Lactrol per volume liquid) as dissolved in the water phase of the prepared biomass material, for example at about at about 5 ppm w/v. In an embodiment using an enzyme to control bacterial growth, lysozyme is preferably used. The lysozyme can come from a commercial source. An exemplary commercially available lysozyme preparation is Lysovin, which is a preparation of the enzyme lysozyme that has been declared permissible for use in food, such as wine.

The enzyme and/or other antibiotic material, if used, can be added independently or in conjunction with one another and/or with the microbe. In certain embodiments, other compounds serving as nutrients to the microbes facilitating and/or providing the volatile organic compound production can also be added as an additive. The following Table 4 provides non-limiting examples of other substances, including antibiotics, which can be added to the solid biomass.

TABLE 4

| Potassium Metabisulfite | Potassium Bicarbonate | FermaSure ® (from Dupont ™) - oxychlorine products including chlorite | Lysovin |
| Thiamin | Magnesium Sulfate | Calcium Pantothenate | Diammonium Phosphate |
| Ammonia | Antibiotics | Lactrol | Biotin |

Yeasts and other microbes that are attached to solids individually, as small aggregates, or biofilms have been shown to have increased tolerance to inhibitory compounds. Not intended to be bound by theory, part of the long-term fermentation may be possible or enhanced by such microbial-to-solids binding. As such, the prepared biomass material that includes the microbe optimized for microbial binding as well as additives that may bind microorganisms can experience a greater extent of fermentation and or efficiency of fermentation. Substances providing and/or facilitating long term fermentation is different from substances that increase the rate of fermentation. In certain embodiments, an increase in the rate of fermentation is not as an important factor as the long-term fermentation, particularly over a period of many weeks or months.

The following provides particular amounts of additives applied to one specific embodiment. If used, the rate and amount of adding an acid varies with the buffering capacity of the particular solid biomass to which the particular acid is added. In a particular embodiment using sulfuric acid, 9.3% w/w sulfuric acid is added at rates of up to about 10 liter/ton wet biomass, for example at about 3.8 liter/ton wet biomass to achieve a pH of about 4.2. In other embodiments, the rate will vary depending on the concentration and type of acid, liquid and other content and buffering capacity of the particular solid biomass, and/or desired pH. In this particular embodiment, Lactrol is added at a rate of about 3.2 g/wet ton of solid biomass. Yeasts or other microbes are added according to the recommended rate from the provider, such as according to the expected sugar content per wet ton. In one particular embodiment, Lallemand stabilized liquid yeast is added at about 18 fl oz per wet ton, and Novozymes Cellic CTec2 is added at about 20 fl oz per wet ton.

In a preferred embodiment, selected additive(s) are added to the solid biomass stream during harvest according to aspects of the invention described above to generate the prepared biomass material. Preferably, the prepared biomass material is transported to a storage facility to allow for conversion of carbohydrates of the prepared biomass material into volatile organic compounds of the desired amount and/or await recovery of the volatile organic compounds. Any suitable transportation method and/or device can be used, such as vehicles, trains, etc, and any suitable method to place the prepared biomass material onto the transportation means. Non-limiting examples of vehicles that can be used to transport the biomass material include end-unloading dump trucks, side-unloading dump trucks, and self-unloading silage trucks. In a preferred embodiment, a silage truck is used. In embodiments using a forage harvester to collect the biomass, transportation of such solid biomass is more efficient than transportation of materials collected by conventional means, such as sugar cane billets, because the bulk density is higher in the solid biomass cut with a forage harvester. That is, materials chopped into smaller pieces pack more densely than materials in billets. In one embodiment, the range of bulk densities in a silage truck varies between about 150 kg/m$^3$ and about 350 kg/m$^3$, for example about 256 kg/m$^3$. Because in certain embodiments, all selected additives are added during harvest, preferably on the harvester, the microbe may begin to interact with the biomass during transportation, and in this way transportation is not detrimental to the overall process.

The biomass, whether prepared or not, is delivered to at least one storage area or facility. The storage facility can be located any distance from the harvest site. Selected additive(s) can be added if they have not been added already or if additional amounts or types need to be further added to generate the prepared biomass material. In a preferred embodiment, the prepared biomass is stored in at least one pile on a prepared surface for a period of time. The facility can incorporate man-made or natural topography. Man-made structures can include existing structures at the site not initially designated for silage, such as canals and water treatment ponds. Non-limiting examples of a prepared surface includes a concrete, asphalt, fly ash, or soil surface. The at least one pile can have any dimension or shape, which can depend on operating conditions, such as space available, amount of biomass, desired storage duration, etc.

The conversion process of fermentable sugars is an exothermic reaction. Too much heat, however, can be detrimental to the conversion process if the temperature is in the lethal range for the microbes in the prepared biomass material. However, in an embodiment using about 700 wet tons of biomass and piling up to about 12 feet, ethanol production and stability were satisfactory. Therefore larger piles will likely not suffer from overheating. In one embodiment, an inner portion of the pile maintains a temperature in a range of about 20° C. to about 60° C. for microbes of all types, including thermophiles. In an embodiment not employing thermophiles, an inner portion of the pile maintains a temperature in a range of about 35° C. to about 45° C.

The prepared biomass material that is stored as at least one pile at the storage facility can also be referred to as a wet stored biomass aggregate. After addition of the selected additive(s), at least a portion of the solid biomass is converted to volatile organic compounds, such as fermentation of sugars into ethanol. In one embodiment, the prepared biomass material is stored for a period of time sufficient to achieve an anaerobiasis environment. In a preferred embodiment, the anaerobiasis environment is achieved in about 24 hours. In another embodiment, the anaerobiasis environment is achieved in more than about 4 hours. In yet another embodiment, the anaerobiasis environment is achieved in up to about 72 hours.

The pile can be free standing or formed in another structure, such as a silage bunker, designed to accept silage, including provisions to collect aqueous runoff and leachate, placement of a tarp over the biomass, and to facilitate both efficient initial silage truck unloading into the bunker as well as removal of the biomass year around. The individual bunkers may be sized at about the size to support annual feedstock requirements of about 700 wet tons to 10,000,000 wet tons or more. For example, the storage facility may have 50 bunkers, where each individual bunker can accept 100,000 wet tons of prepared biomass material for a total of a maximum of about 5 million wet tons of stored material at any one time. In a preferred embodiment where ethanol is the volatile organic compound of choice, about 14 gallons to about 16 gallons of ethanol is recovered per one wet ton of prepared biomass material. The provided numbers are exemplary and not intended to limit the amount of prepared biomass material a storage facility can accommodate.

In a particular embodiment, the storage pile further includes a leachate collection system. In one embodiment, the collection system is used to remove leachate collected from the storage pile. For example, the leachate collection system can be adapted to remove liquid from the pile at certain points during the storage period. In another embodiment, the leachate collection system is adapted to circulate the liquid in the storage pile. For example, circulation can involve taking at least a portion of the recovered liquid and routing it back to the pile, preferably at or near the top portion. Such recirculation allows for longer retention time of certain portions of the liquids in the pile, even as the recovery phase of the prepared biomass material begins and portions of the non-liquid component of the prepared biomass material are sent to the recovery unit. The longer retention time results in longer microbial reaction time, and hence, higher concentrations of organic volatile compounds, such as ethanol.

Any suitable leachate collection system known to those skilled in the art can be employed as described. In a particular embodiment, the leachate collection system comprises at least one trough along the bottom of the pile, preferably positioned near the middle, of the storage pile or bunker if one is used, where the storage pile is prepared at a grade designed to direct liquid from the prepared biomass material to the trough and out to a desired collection receptacle or routed to other applications.

In another embodiment, the leachate collection system comprises one or more perforated conduits, preferably pipes made of polyvinyl chloride (PVC), that run along the bottom of the pile to allow the liquid collected in the conduits to be directed away from the pile.

In one embodiment, as the prepared biomass material is added to the bunker or laid on top of the prepared surface, a tractor or other heavy implement is driven over the pile repeatedly to facilitate packing. In one embodiment, the packing ranges from about 7 lbs/ft$^3$ to about 50 lbs/ft$^3$ per cubic foot for the prepared biomass material. In a preferred embodiment, the packing is from about 30 lbs/ft$^3$ to about 50 lbs/ft$^3$, particularly about 44 lbs/ft$^3$. In one embodiment, the compacting of the prepared biomass material in a pile facilitates and/or allows an anaerobiasis environment to be achieved in the preferred time periods described above. In another embodiment, after the packing is performed or during the time the packing is being performed, an air impermeable membrane is placed on the pile, typically a fit for purpose plastic tarp. In a particular embodiment, the tarp is placed on the pile as soon as is practical. For instance, the tar is placed on the pile within a 24-hour period.

In one embodiment, the prepared biomass material is stored for at least about 24 hours and preferably at least about 72 hours (or 3 days) to allow for production of volatile organic compounds, such as ethanol. In one embodiment, the prepared biomass material is stored for about three days, preferably ten days, more preferably greater than ten days. In one embodiment, the time period for storage of the prepared biomass is about 1 day to about 700 days, preferably about 10 to 700 days. In another embodiment, the biomass material is stored for up to about three years. In one embodiment, the prepared biomass material is stored for a time period sufficient to allow a conversion efficiency of sugar to at least one volatile organic compound of at least about 95% of the theoretical production efficiency as calculated through a stoichiometric assessment of the relevant biochemical pathway. In another embodiment, the prepared biomass material is stored for a time period sufficient to allow a calculated conversion efficiency of sugar to at least one volatile organic compound of at least about 100%. In yet another embodiment, the prepared biomass material is prepared with certain additives, such as enzymes, that allow a calculated conversion efficiency of sugar to at least one volatile organic compound of up to about 150% of the theoretical value based on the initial amount of available fermentable sugars. Not intended to be bound by theory, it is believed that, at or above 100% efficiency, the volatile organic compound(s) are produced from both the initially available fermentable sugars and fermentable sugars from cellulosic or other polymeric material in the prepared biomass material, which can be achieved by enzymatic hydrolysis or acid hydrolysis facilitated by certain additive(s) applied to the biomass.

The produced volatile organic products, such as ethanol, remain stable in the stored prepared biomass material for the duration of the storage period. In particular, the prepared biomass material can be stored up to 700 days without significant degradation to the volatile organic compounds. "Significant" in this context refers at least to within the margin of error when measuring the amount or concentration of the volatile organic compounds in the prepared biomass material. In one embodiment, the margin of error is 0.5%. It has been demonstrated that ethanol remains stable in the pile after at least about 330 days with no significant ethanol losses observed. This aspect of embodiments of the present invention is important because it provides for at least eight months of stable storage, which enables year-round VOCs production and recovery with a harvest window of only about four months. Embodiments of the invention provide significant advantages over the conventional just-in-time processing that would only be able to operate during the four months harvest window per year. That is, embodiments of the invention allow a plant to operate year-round using only a four-month harvest window, thereby reducing capitals cost for a plant of the same size as one used for just-in-time processing.

Also, in an embodiment employing a tarp, it is envisioned that placing soil or other medium around and on the tarp edges to 1) provide weight for holding the tarp down; and also 2) to act as a biofilter of the off-gas from the pile. In such an embodiment, biofilters are efficient for organics and carbon monoxide detoxification/degradation. The prepared biomass material can also be stored as compressed modules, drive over piles, bunkers, silos, bags, tubes, or wrapped bales or other anaerobic storage system.

In one embodiment, the off-gas stream from a pile of prepared biomass material was monitored, and it was found that only small levels of organics, and also very low levels of nitrogen oxides, were present. For example, Tables 5.1, 5.2, and 5.3 below show the analysis of various off-gas samples collected during the storage phase of one implementation of certain embodiments of the invention. The designation "BDL" refers to an amount below detectable limit. Summa and Tedlar refer to gas sampling containers commercially available.

TABLE 5.1

| Container type | Container ID | % $H_2$ | % $O_2$ | % $N_2$ | % $CH_4$ | % $CO_2$ | % $H_2O$ | Normalized $CO2$ |
|---|---|---|---|---|---|---|---|---|
| Tedlar bag | A | BDL | 1.72 | 7.84 | BDL | 95.90 | 5.23 | 85.21 |
| Tedlar bag | B | BDL | 2.30 | 9.12 | BDL | 89.97 | 5.97 | 82.62 |
| Tedlar bag | C | BDL | 0.71 | 3.57 | BDL | 97.45 | 5.54 | 90.18 |
| Tedlar bag | D | BDL | 0.72 | 3.18 | BDL | 97.50 | 5.97 | 90.14 |
| Tedlar bag | E | BDL | 1.86 | 7.24 | BDL | 91.75 | 7.64 | 83.26 |
| Summa Container | EQ #8 | 0.01 | 5.74 | 22.14 | 0.07 | 73.74 | 5.28 | 66.84 |
| Summa Container | EQ #13 | 0.09 | 3.28 | 12.89 | 0.33 | 84.48 | 5.66 | 78.18 |
| Summa Container | EQ #16 | 0.12 | 3.30 | 13.01 | 0.12 | 84.65 | 4.99 | 78.70 |

TABLE 5.2

| Container type | Container ID | % $O_2$ | ppmv CO | % $CO_2$ | ppmv HC | ppmv NO | ppmv $NO_2$ | ppmv $NO_X$ | ppmv $SO_2$ |
|---|---|---|---|---|---|---|---|---|---|
| Tedlar bag | A | 1.6 | 13 | 72.7 | 104 | 3.8 | 1.90 | 5.70 | BDL |
| Tedlar bag | B | 4.4 | 19 | 66.2 | 739 | 2.5 | 122.90 | 125.40 | 6 |
| Tedlar bag | C | 0.6 | 29 | 75.3 | 158 | 8.9 | 27.20 | 36.10 | 4 |
| Tedlar bag | D | 0.6 | 35 | 75.7 | 222 | 7.9 | 56.50 | 64.40 | 5 |
| Tedlar bag | E | 4.1 | 35 | 66.8 | 423 | 3.0 | 20.30 | 23.90 | 4 |

TABLE 5.3

| Container type | Container ID | ppmv CH2O | ppmv C2H4O | ppmv methanol | ppmv 2-propanol | ppmv ethanol | ppmv propanol |
|---|---|---|---|---|---|---|---|
| Tedlar bag | A | 386 | 870 | 63.4 | 0.593 | 78.5 | BDL |
| Tedlar bag | B | BDL | 1299 | 678 | 0.186 | 1065 | 15.2 |
| Tedlar bag | C | 18.2 | 590 | 89.2 | 2.784 | 171 | 6.098 |
| Tedlar bag | D | BDL | 941 | 170 | 3.031 | 264 | 7.648 |
| Tedlar bag | E | BDL | 819 | 389 | 2.512 | 634 | 11.3 |

Embodiments of the present invention, although relatively uncontained in the bunker, should be environmentally benign. Even so, certain aspects of the present invention fit well with using soil or other media as a biofilter placed around and on the bunkers because the escape of gas from under the tarp is radial in nature. As such, the vapors have a higher amount of surface area in contact with the edges of the pile. In embodiments using a biofilter, vapor phase releases pass through the biofilter (such as soil or compost) placed near the edge mass before entering into the atmosphere. The biofilter retains many potential environmental pollutants and odors released by the storage pile, and it eliminates or greatly reduces the potentially harmful off-gases released from the storage pile.

In one embodiment, the prepared biomass material is stored until it contains no more than about 80 wt % liquid. The prepared biomass material is stored until it contains at least about 4 to about 5% higher than initial content. At this stage, the wet stored biomass aggregate is not considered "beer" yet since it still contains over about 20% solids. In one embodiment, the prepared biomass material is stored until it contains between about 2 wt % and about 50 wt % ethanol, and preferably between about 4 wt % and about 10 wt % ethanol. The balance of the liquid is primarily water but can contain many other organic compounds, such as acetic acid, lactic acid, etc.

Embodiments of the present invention allow the solid biomass to be harvested in a much shorter harvest window than typical sugar cane juicing operations, which allows for 1) a much larger geographic area where the facilities could be placed,
2) harvest of the crop when the crop has its highest yield potential,
3) harvest of the crop at its highest sugar concentration potential,
4) shorter harvest window still economical, and
5) decoupling the need for taking the juice from the biomass for fermentation.

The preparation of the biomass material of embodiments of the invention can also be generally referred to as solid state fermentation.

VOC Recovery

Once the prepared biomass material has been stored for the desired amount of time and/or contains a desired concentration of volatile organic compounds, such as ethanol, it can be routed to the VOC recovery system for recovery of particular volatile organic compounds. The recovery system and storage facility can be located any distance from one another. Embodiments of systems and methods described herein allow flexibility in the geographical location of both and their locations relative to each other. In a particular embodiment, the recovery system is located about 0.5 to about 2 miles from the storage facility. Any suitable method and/or equipment can be used to transfer the prepared biomass material from the storage facility to the recovery system. In one embodiment, a feed hopper is used. In one embodiment, a silage facer, a front end loader or payloader, a sweep auger or other auger system can be used to place the prepared biomass material into the feed hopper. The material can be placed directly into the feed hopper or it can be transferred to by conveyer system, such as belt system. The feed hopper containing the prepared biomass material can then be driven to the recovery system.

The recovery system is solventless and uses a superheated vapor stream to vaporize the liquid in the prepared biomass material into a gas component, which can then be collected. A super-heated vapor is a vapor that is heated above its saturation temperature at the pressure of operation. In a preferred embodiment, after the recovery system reaches steady state, the superheated vapor stream comprises only vapor previously evaporated from the prepared biomass material, so that no other gas is introduced, thereby reducing the risk of combustion of the volatile organic compounds and/or dilution of the recovered product stream of volatile organic compounds. A portion of the vapor is removed as product and the remainder is recycled back for use in transferring heat to fresh incoming prepared biomass material. The remaining solid component is discharged from the system and can have various subsequent uses. The super-heated vapor directly contacts the biomass transferring energy and vaporizing the liquid present there. The heat or thermal energy source does not directly contact the prepared biomass material. Thus, the VOC recovery system can also be described as providing "indirect" heat contact.

To provide solventless recovery of volatile organic compounds, the recovery system comprises a compartment that allows superheated vapor to flow in a continuous manner, i.e., as a stream. In one embodiment, the compartment has a loop shape. In another embodiment, the compartment comprises a rotating drum. The compartment has an inlet through which the prepared biomass material can enter. In one embodiment, the inlet comprises a pressure tight rotary valve, plug screw, or other similar device, which can assist in separating the prepared biomass material to increase the surface area exposed to the superheated vapor stream.

In yet another embodiment, the system comprises a dewatering mechanism to remove at least a portion of the liquid in the prepared biomass material before the liquid is vaporized. The liquid removal can occur before and/or while the prepared biomass material enters the compartment. The liquid from the prepared biomass material contains at least one volatile organic compound, which can be recovered by further processing the liquid, such as feeding the liquid to a distillation column. The liquid can be routed directly to further processing unit, such as a distillation column. Alternatively or in addition to, the system further includes a collection unit to collect the liquid removed from the prepared biomass material. Any portion of the collected liquid can then be further processed.

In one embodiment, the dewatering mechanism comprises a component adapted to squeeze the liquid from the prepared biomass material. In such an embodiment, the squeezing can be performed while the prepared biomass material is being fed into the compartment. For instance, the inlet can comprise a squeezing mechanism to squeeze liquid from the prepared biomass material as it is introduced into the compartment. Alternatively or in addition to, the squeezing can be performed separately before the prepared biomass material enters the compartment. A non-limiting example of such a squeezing mechanism is a screw plug feeder.

In one embodiment, the liquid removal mechanism comprises a mechanical press. Non-limiting examples of types of mechanical presses include belt filter presses, V-type presses, ring presses, screw presses and drum presses. In a particular embodiment of a belt filter press, the prepared biomass material is sandwiched between two porous belts, which are passed over and under rollers to squeeze moisture out. In another particular embodiment, a drum press comprises a perforated drum with a revolving press roll inside it that presses material against the perforated drum. In yet another embodiment, in a bowl centrifuge, the material enters a conical, spinning bowl in which solids accumulate on the perimeter.

The compartment provides a space where the superheated vapor stream can contact the prepared biomass material to vaporize the liquid from the prepared biomass material. The vaporization of at least a portion of the liquid provides a gas component and a solid component of the prepared biomass material. The system further comprises a separating unit where the solid component of the prepared biomass material can be separated from the gas component, so each component can be removed as desired for further processing. In one embodiment, the separating unit comprises a centrifugal collector. An example of such centrifugal collector is high efficiency cyclone equipment. In a preferred embodiment, the separating unit also serves as an outlet for the solid component. For example, the separating unit can discharge the solid component from the solventless recovery system. There is a separate outlet for the gas component where it can exit the system for further processing, such as distillation. In one embodiment, the separating unit is further coupled to a second pressure tight rotary valve or the like to extrude or discharge the solid component. In one embodiment, the superheated vapor is maintained at a desired or target temperature above its saturation temperature by a heat exchange component coupled to a heat source where the superheated vapor does not contact the heat source. The heat transfer between the heat source and the system occurs via convection to the superheated vapor. In one embodiment, the heat source can include electrical elements or hot vapors through an appropriate heat exchanger. In one embodiment, the operating pressure is in a range from about 1 psig to about 120 psig. In a preferred embodiment, the operating pressure is in a range from about 3 psig to about 40 psig. In a particularly preferred embodiment, the system is pressurized at an operating pressure of about 60 psig to force the vapor component from the system.

In one embodiment, at start up of the recovery system, the prepared biomass material is introduced into the compartment via the inlet. Steam is initially used as the superheated vapor to initially vaporize the liquid in the prepared biomass material. The superheated vapor continuously moves through the compartment. When the prepared biomass material enters the superheated vapor stream, it becomes fluidized where it flows through the compartment like a fluid. As the prepared biomass material is introduced, it comes into contact with the superheated vapor stream. Heat from the superheated vapor is transferred to the prepared biomass material and vaporizes at least a portion of the liquid in the prepared biomass material and is separated from the solid component, which may still contain moisture. The gas component contains volatile organic compound(s) produced in the prepared biomass material. In a preferred embodiment, as liquid from the prepared biomass material begins to vaporize, at least a portion of the vaporized liquid can be recycled in the system as superheated fluid. That is, during any one cycle, at least a portion of the vaporized liquid remains in the compartment to serve as superheated vapor instead of being collected for further processing, until the next cycle where more prepared biomass material is fed into the system.

In a preferred embodiment, during the initial start up procedure, the superheated fluid can be purged as needed, preferably continuously (intermittently or constantly), until steady state is achieved where the superheated vapor comprises only vaporized liquid of the prepared biomass material. The gas component and solid component can be collected via the respective outlet. Heat can be added continuously (intermittently or constantly) to the system via the heat exchanger coupled to the heat source to maintain the temperature of the superheated vapor, to maintain a desired operating pressure in the system, or to maintain a target vaporization rate. Various conditions of the system, such as flow rate of the superheated vapor stream, pressure, and temperature, can be adjusted to achieve the desired liquid and/or volatile organic compounds removal rate.

In one embodiment, the collected gas component is condensed for further processing, such as being transferred to a purification process to obtain a higher concentration of the volatile organic compound(s) of choice. In a preferred embodiment, the collected gas component is fed directly into a distillation column, which provides savings of energy not used to condense the gas component. In another embodiment, the gas component is condensed and fed to the next purification step as liquid.

In one embodiment, before entering the recovery phase, the prepared biomass material has an initial liquid content of about at least 10 wt % and up to about 80 wt % based on the biomass material. In a particular embodiment, the initial liquid content is at least about 50 wt % based on the biomass material. In one embodiment, the initial liquid content comprises from about 2 to 50 wt %, and preferably from about 4 to 10 wt % ethanol based on the initial liquid content.

In one embodiment, the solid component collected contains from about 5 wt % to about 70 wt %, and preferably from about 30 wt % to about 50 wt %, liquid depending on the ethanol removal target. In another component, the collected gas component contains between about 1 wt % and about 50 wt % ethanol, preferably between about 4 wt % and about 15 wt % ethanol. In one embodiment, the recovery system recovers from about 50% to about 100% of the volatile organic compounds contained in the prepared biomass material. The residence time of the prepared biomass varies based on a number of factors, including the volatile organic compound removal target. In one embodiment, the residence time of the prepared biomass material in the compartment is in a range of about 1 to about 10 seconds. In one embodiment, the recovery system can be operated between about 0.06 barg and about 16 barg. The term "barg" refers to bar gauge as understood by one of ordinary skill in the art, and 1 bar equals to 0.1 Mega-Pascal. In one embodiment, the gas in the recovery system has a temperature in a range of about 100° C. to about 375° C., particularly from about 104° C. to about 372° C., and the solid component exiting the system has a temperature of less than about 50° C. The collected solid component can be used in other applications. Non-limiting examples include animal feed, feed for a biomass burner to supply process energy or generate electricity, or further converted to ethanol by means of a cellulosic ethanol process (either re-ferment in a silage pile, or feed to a pre-treatment unit for any cellulosic ethanol process) or a feed for any other bio-fuel process requiring ligno-cellulosic biomass.

The operating conditions of the solventless recovery system include at least one of temperature, pressure, flow velocity, and residence time. Any one or combination of these conditions can be controlled to achieve a target or desired removal target, such as the amount of the initial liquid content removed or the amount of the liquid remaining in the separated liquid component exiting the recovery system. In one embodiment, at least one operating condition is controlled to achieve removal of about 10-90 wt %, preferably about 45-65 wt %, and more preferably about 50 wt %, of the initial liquid content.

In a preferred embodiment, increasing the temperature of the system at constant pressure will cause the liquid in the biomass to be vaporized more quickly and thus for a given residence time will cause a higher percentage of the liquid in the biomass to be evaporated. The vapor flow rate exiting the system has to be controlled to match the rate of vaporization of liquid from the biomass in order to achieve steady state and can also be used as a mechanism to control the system pressure. Increasing the system pressure will cause more energy to be stored in the vapor phase in the system which can then be used to aid in further processing or to help move the vapor to the next downstream processing unit. Increasing the biomass residence time in the system causes more heat to be transferred from the vapor phase to the biomass resulting in more liquid being vaporized.

In a specific exemplary embodiment, the recovery system comprises a closed loop pneumatic superheated steam dryer, which can be obtained from commercially available sources. In one embodiment, the closed loop pneumatic superheated steam dryer is an SSD™ model of GEA Barr-Rosin Inc. Other suitable commercially available equipment include the Superheated Steam Processor, SSP™ from GEA Barr-Rosin Inc, the Ring Dryer from several companies including GEA Ban-Rosin Inc. and Dupps; the Airless Dryer from Dupps; the QuadPass™ Rotary Drum Dryer from DuppsEvactherm™, Vacuum Superheated Steam Drying from Eirich; the rotary drum dryer using superheated vapor from Swiss Combi Ecodry; and the airless dryer from Ceramic Drying Systems Ltd.

Still other types of indirect dryers that could serve as the volatile organics recovery unit for this process are batch tray dryers, indirect-contact rotary dryers, rotating batch vacuum dryers, and agitated dryers. The basic principle for these dryers is that they will be enclosed and attached to a vacuum system to remove vapors from the solids as they are generated (also by lowering the pressure with the vacuum the volatiles are removed more easily). The wet solids contact a hot surface such as trays or paddles, the heat is transferred to the wet solids causing the liquids to evaporate so they can be collected in the vacuum system and condensed.

FIG. 1 illustrates an exemplary VOC recovery system and process employing a superheated steam dryer, referenced as system 100. In a particular embodiment, the superheated steam dry can be obtained from GEA Ban-Rosin Inc. In FIG. 1, prepared biomass material 1 containing ethanol and/or other VOCs following solid state fermentation in the silage piles is fed into compartment 3 through input 2. In the particular embodiment shown, input 2 comprises a screw extruder. As shown in FIG. 1, at least a portion of the liquid of the prepared biomass material 1 is removed prior to entering compartment 3. The dewatering mechanism can be a screw plug feeder through which the prepared biomass material 1 passes. At least a portion of the liquid removed from biomass material 1 can be routed directly to distillation step 11 via stream 15 without going through recovery system 100. Optionally, a delumper can be coupled to the output of the dewatering mechanism can be used to facilitate introduction of the dewatered biomass material into compartment 3.

Figure 3:
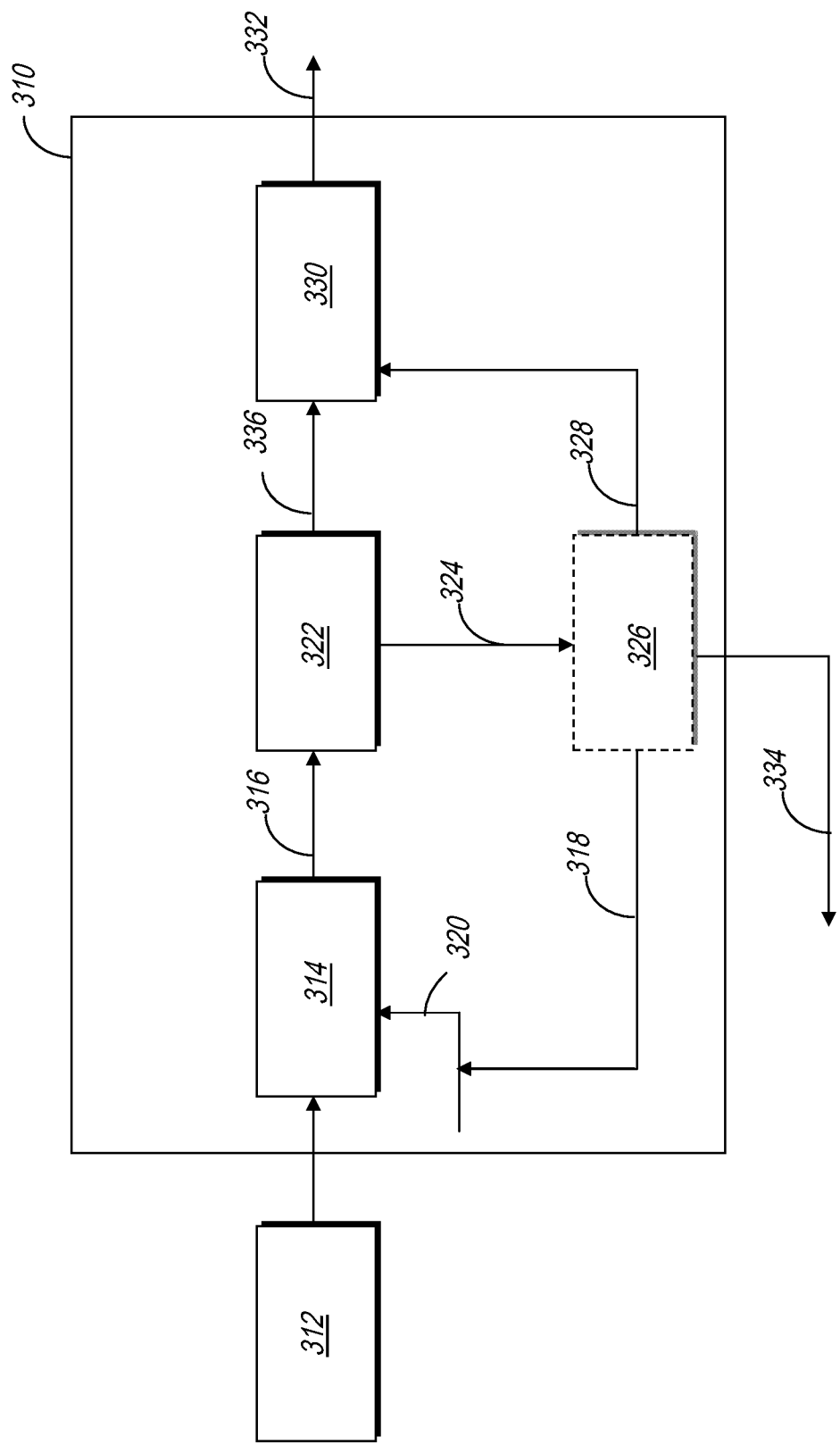
FIG. 3 is a diagram of one embodiment to convert a solid component to a higher hydrocarbon according to certain aspects of the present invention.

Referring to FIG. 1, recovery system 100 comprises compartment 3, which can be pressurized, shown as a conduit that has an appropriate diameter, length and shape, adapted to provide the desired operating conditions, such as residence time of prepared biomass material 1, heat transfer to the superheated vapor, and operating pressure and temperature. After entering compartment 3, during steady state operation, prepared biomass material 1 contacts superheated vapor flowing through system 100 at a desired or target temperature and becomes fluidized. As described above, in a preferred embodiment, the superheated vapor, or at least a portion thereof, is vapor component obtained from prepared biomass materials previously fed into system 100 for VOC recovery. The fluidized biomass flows through compartment 3 at a target flow rate and remains in contact with the superheated vapor for a target residence time sufficient to evaporate the desired amount of liquid from prepared biomass material 1. In the embodiment shown, the flow of the superheated vapor and prepared biomass material 1 through system 100 is facilitated by system fan 14. System 100 can have one or more fans. The flow rate or velocity of the superheated vapor and biomass material 1 can be controlled by system fan 14. Biomass material 1 flows through compartment 3 and reaches separating unit 4, which is preferably a cyclone separator, where a vapor component and a solid component of biomass material 1 are separated from each other. As shown, the vapor component is routed away from the solid component via overhead stream 5 and the remaining portion of biomass material 1 is considered a solid component, which is discharged from separating unit 4 as solid component 7, preferably by screw extruder 6. At least a portion of the discharged solid component 7 can be used as animal feed, burner fuel, or biomass feedstock for other bio-fuels processes. For example, at least a portion of solid component 7 can serve as feedstock for process 310 that converts carbohydrate to higher hydrocarbons using thermocatalytic chemistry. Process 310 is illustrated in FIG. 3 and correspondingly further discussed below. Referring to FIG. 1, a portion of the vapor component, referenced as stream 8, is retained and recycled as a portion of the superheated vapor used to vaporize newly introduced prepared biomass material. In the embodiment shown, the retained vapor component in stream 8 is routed through heat exchanger 9 to heat it to the target operating temperature. The heat source can include steam, electricity, hot flue gases or any other applicable heating source known to those skilled in the art.

In a preferred embodiment, the temperature is controlled such that the pressure in the system is maintained at the target and there is adequate energy present to evaporate the desired amount of liquid. The pressure can also be controlled by the flow rate of the superheated vapor stream and the heat input to heat exchanger 9. Preferably, recovery system 100 operates continuously where prepared biomass material 1 is continuously fed at a desired rate, and vapor component 10 and solid component 6 are continuously removed at a continuous rate. In a preferred embodiment, "fresh" vapor component 8 from one run is retained continuously at a target rate to be used as the superheated vapor stream for the next run. Any of these rates are adjustable to achieve the desired operating conditions. As mentioned, system fan 14 circulates the superheated vapor stream through system 100 and can be adjusted to obtain the target flow rate or velocity.

Referring to FIG. 1, the remaining portion of vapor component stream 5, represented as numeral 10 is routed to a distillation step 11. Depending on the distillation configuration, vapor component portion 10 may be condensed before further purification or preferably fed directly into the distillation column as a vapor. In a preferred embodiment, the distillation product from distillation step 11 has an ethanol content of about 95.6 wt % ethanol (the ethanol/water azeotrope), which can further be purified to above about 99 wt % using common ethanol dehydration technology, which is shown as step 12. The final ethanol product 13 will then typically be used as a biofuel for blending with gasoline.

Figure 2:
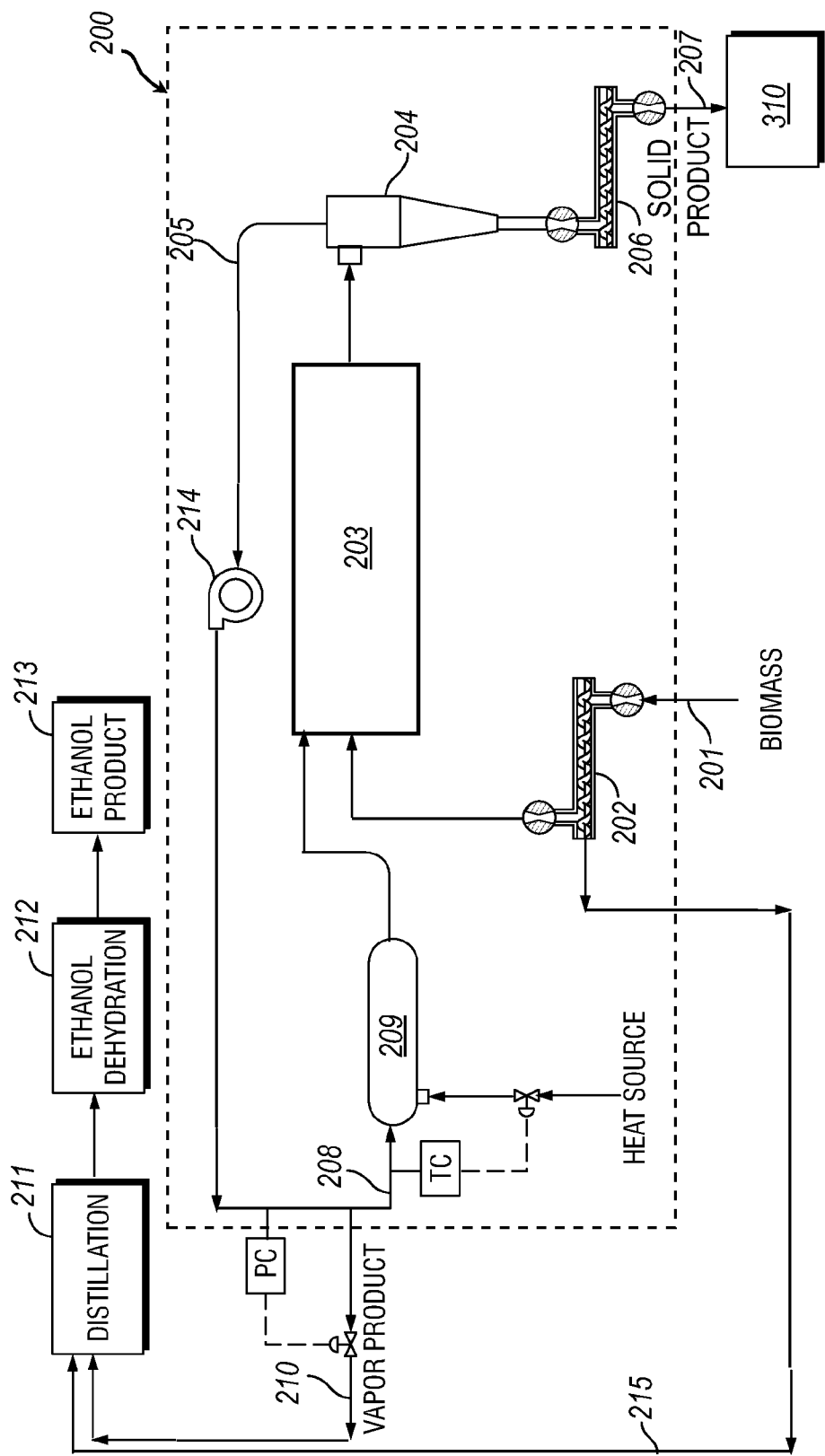
FIG. 2 is a diagram of another embodiment to process biomass material according to certain aspects of the present invention.

FIG. 2 illustrates another exemplary recovery system and process employing a superheated steam dryer, referenced as system 200 that is representative of the Ring Dryer provided by various manufacturers. Prepared biomass material 201 is fed into system 200 through input 202, which preferably comprises a screw extruder. In one embodiment, least a portion of the liquid of the prepared biomass material 201 is removed prior to entering system 200. The dewatering mechanism can be a screw plug feeder through which the prepared biomass material 201 passes. At least a portion of the liquid removed from biomass material 201 can be routed directly to distillation step 211 via stream 215 without going through recovery system 200. Optionally, a delumper can be coupled to the output of the dewatering mechanism can be used to facilitate introduction of the dewatered biomass material into compartment 203.

Referring to FIG. 2, recovery system 200 comprises compartment 203, which preferably comprises a rotating drum that provides the target operating conditions for VOC recovery, including residence time of prepared biomass material 201, heat transfer to the superheated vapor, and operating pressure and temperature. After entering compartment 203, during steady state operation, prepared biomass material 201 contacts superheated vapor flowing through system 200 at the operating temperature and flow rate and becomes fluidized. As described above, in a preferred embodiment, the superheated vapor, or at least a portion thereof, is the vapor component obtained from prepared biomass material previously fed into system 200 for VOC recovery. The fluidized biomass flows through compartment 203 at a target flow rate and remains in contact with the superheated vapor for the target residence time to achieve the target vaporization of liquid from the biomass. The fluidized biomass then reaches separating unit 204, which is preferably a cyclone separator, where the vapor component and solid component are separated from each other. As shown, the vapor component is routed away from the solid component through overhead stream 205, and solid component 207 is discharged from separating unit 204. As shown, solid component 207 exits system 100 via extruder 206. At least a portion of solid component 207 can enter further processing system 310, which is further described below with respect to FIG. 3. Solid component 207 can be routed directly to further processing system 310 for a continuous operation of the recovery system and the further processing system. In addition to, or alternatively, solid component 207 can be transported to further processing system 310. A portion of the vapor component, referenced as stream 208, is retained and recycled as a portion of the superheated vapor used to vaporize newly introduced prepared biomass material. As shown, retained vapor component 208 is routed through heat exchanger 209 to heat it to the desired or target temperature. The heat source or thermal energy source can include steam, electricity, hot flue gases or any other desired heating source. As shown, hot flue gas is used. The temperature is controlled such that the pressure in the system is maintained at the target and there is adequate energy present to evaporate the desired amount of liquid. The pressure can also be controlled by the flow rate of the superheated vapor stream and the heat input to heat exchanger 209.

Referring to FIG. 2, the remaining portion of vapor component stream 205, represented as numeral 210 is routed to a distillation step. Depending on the distillation configuration, vapor component portion 210 may be condensed before further purification or preferably fed directly into the distillation column as a vapor. The product from the distillation step can further be concentrated using known processes.

Preferably, recovery system 200 operates continuously where prepared biomass material 201 is continuously fed at a desired rate, and vapor component 210 and solid component 206 are continuously removed at a continuous rate. In a preferred embodiment, "fresh" vapor component 208 from one run is retained continuously at a target rate to be used as the superheated vapor stream for the next run. All these rates are adjustable to achieve the desired operating conditions. System fan 214 creates a circulating loop of superheated vapor stream and can be adjusted to obtain the target flow rate.

By using a solventless recovery system according to aspects of the present invention, the points of heat transfer in the system, i.e., addition of heat to the system and heat transfer to the prepared biomass material, take place in the vapor phase in a preferred embodiment, which provides an advantage cause vapor phase heat transfer (convection) is more efficient than solid phase heat transfer (conduction) in the prepared biomass material, which is a bad conductor because it has insulating properties. As mentioned above, in certain embodiments, once steady state is reached no vapor other than that vaporized from the liquid of the prepared biomass material contacts the solid component and gas component of the prepared biomass material in the system, which prevents or reduces dilution that would come from the addition of process steam or other vapor to replenish the superheated vapor stream. The collected gas component can be fed directly to a distillation column for separation of the desired volatile organic compound(s), which can provide significant energy savings. The advantage of this system is that the vapors that contact the wet solids are only those vapors that have been previously removed from the solids so that there is no dilution or explosion risk, etc.

Conversion to Hydrocarbons

Referring to FIGS. 1 and 2, at least a portion of the solid component, such as solid components 7 and component 207, discharged from the recovery system, such as systems 100 and 200, can serve as feedstock to further processing system 310 and be further processed to produce higher hydrocarbons. The solid component serving as biomass feedstock to further processing system 310 may be referred to as "solid component feedstock," "solid component biomass," or simply as "feedstock" or "biomass." Further processing system 310 converts carbohydrate to higher hydrocarbons suitable for transportation fuels and industrial chemicals. In a preferred embodiment, the further processing system, such as system 310, is located near the VOC recovery system, such as system 100 or 200, and is coupled to the VOC recovery system so that at least a portion of the solid component discharged from the recovery system is directly routed to further processing system 310, which is preferably operated in a continuous or semi-continuous flow mode. In that preferred embodiment, the solid component feedstock is in an entrained system where it is already flowing in an engineered system instead of requiring a mechanism to take it from storage and introduce it to the further processing system. Further, embodiments that couple the VOC recovery system to the further processing system can allow for production of volatile organic compounds, hydrocarbons, and other chemicals from one site, which reduces storage, handling, and transportation costs associated with other feedstock sources, which are not already in an entrained system. Such embodiments can also provide a continuous supply of feedstock that is already particle size reduced in contrast to conventional feedstock that often requires storage, transportation, and/or size reduction at or prior to arriving at the plant for processing to hydrocarbons, which reduces the particular associated costs. Alternatively or in addition, the solid component can be transported to other further processing systems located at a different location. The solid component can be pelletized or further formatted to facilitate transport and/or reduce transportation costs. In embodiments of the invention, the solid component is already particle size reduced, which reduces the cost and difficulties of pelletization or other formatting processes as compared to other feedstock sources.

In certain embodiments, the higher hydrocarbons produced can be useful in forming transportation fuels, such as synthetic gasoline, diesel fuel, and jet fuel, as well as industrial chemicals. As used herein, the term "higher hydrocarbons" refers to hydrocarbons having an oxygen to carbon ratio less than the oxygen to carbon ratio of at least one component of the solid component feedstock. As used herein the term "hydrocarbon" refers to an organic compound comprising primarily hydrogen and carbon atoms, which is also an unsubstituted hydrocarbon. In certain embodiments, the hydrocarbons of the invention also comprise heteroatoms (i.e., oxygen or sulfur) and thus the term "hydrocarbon" may also include substituted hydrocarbons.

In certain embodiments, the further processing system uses one or more thermocatalytic reactions to form oxygenated intermediate products that can be further subject to another reaction to form higher hydrocarbons. Aqueous phase and/or organic phase solvent can be used for the one or more thermocatalytic reactions. The term "aqueous phase" refers to a liquid phase that can be diluted by water at 1:1 or greater water to liquid-phase ratio, without separating into a second liquid phase. The second liquid phase is defined as a phase having an interfacial tension greater than zero relative to the first phase. Second phase formation can be identified via formation of a liquid-liquid interface which reflects and refracts light, sound, or other waves, for two phases which may separate via density difference, or remain mixed as an emulsion. If a second liquid phase forms upon addition of water at greater than about 5 weight percent relative to the total mixture, the phase having the highest water concentration is designated as the "aqueous phase", with the other phase called the "organic phase." In a particular embodiment, the thermocatalytic reactions comprise formation of oxygenated intermediate products via reforming, hydrogenolysis, or hydrodeoxygenation reaction (collectively hydrocatalytically treated).

For "organic phase hydrocatalytic" processing, the reaction is conducted with an organic solvent which if mixed with water at greater than 1:1 mass ratio, would separate into an organic hydrocarbon-rich phase and an aqueous phase. The organic phase must solubilize some water to effect digestion and "reforming" reactions. A lower limit of about 1 wt % solubility of water in the organic solvent phase at reaction temperatures defines a solvent phase suitable for "hydrocatalytic treatment."

In a particular embodiment, the further processing comprises digestion of the solid component feedstock and hydrocatalytically treating the digested solid component feedstock. The digestion preferably comprises contacting the biomass feedstock with a digestive solvent in a digestion system to form an intermediate stream comprising soluble carbohydrates. The term "soluble carbohydrates" refers to oligosaccharides and monosaccharides that are soluble in a digestive solvent and that can be used as feedstock to the hydrocatalytic reaction (e.g., pentoses and hexoses). The digestion system may have one or more digester(s). The hydrocatalytic treatment comprises contacting the intermediate stream with a catalyst capable of activating molecular hydrogen (hydrocatalytic treatment) to form a hydrocatalytically treated mixture comprising a plurality of oxygenated hydrocarbon molecules, where the catalyst comprises a metal. The catalyst can also be referred to as a molecular hydrogen activating catalyst. The contact with the catalyst can be done under aqueous phase or organic phase hydrothermal conditions. Examples of such process and catalyst are described in U.S. Application Publication No. US20110154722 and US20120317872, and U.S. application Ser. No. 13/663,163, the disclosures of which are incorporated herein in their entirety.

The oxygenated hydrocarbon molecules or oxygenated intermediates comprise polyols, alcohols, ketones, aldehydes, and other mono-oxygenated reaction products. These products can be further treated to form higher hydrocarbons for use in fuel blends. In some embodiments, at least a portion of the oxygenated intermediates are recycled within the further processing to form an in situ generated portion of the digestive solvent used in the digestion process. The term "in situ" as used herein refers to a component that is produced within the overall process; it is not limited to a particular reactor for production or use and is therefore synonymous with an in-process generated component. This recycle saves costs in terms of the amount of solvent used, which can be used to extract nitrogen, sulfur, and optionally phosphorus compounds from the feedstock. The recycle can also increase the amount of carbohydrates extracted from the solid component feedstock.

In some embodiments, the reactions described are carried out in any system of suitable design, including systems comprising continuous-flow, batch, semi-batch or multi-system vessels and reactors. One or more reactions or steps may take place in an individual vessel and the process is not limited to separate reaction vessels for each reaction or digestion. In some embodiments the system of the invention utilizes a fluidized catalytic bed system. Preferably, embodiments of the invention are practiced using a continuous-flow system at steady-state equilibrium.

Each reactor or vessel preferably includes an inlet and an outlet adapted to remove the product stream from the reactor or vessel. In some embodiments, the reactor or vessel in which at least some digestion occurs may include additional outlets to allow for the removal of portions of the reactant stream. In some embodiments, the reactor or vessel in which at least some digestion occurs may include additional inlets to allow for additional solvents or additives.

With other conventional biomass feedstock sources, before treatment with the digestive solvent, the untreated conventional biomass feedstock typically need to be washed and/or reduced in size (such as chopping, crushing or debarking) to a convenient size to aid in moving the biomass or mixing and impregnating the chemicals in the digestive solvent. The solid components generated by various embodiments of the invention eliminate or minimize the need for such washing and/or reduction in size for effective digestion and further reactions, thereby reducing costs, improving efficiency, and allowing for ease of integration of systems, such as going from VOC recovery into thermocatalytic reaction of the solid product discharged from the VOC recovery.

The digestion step may occur in any contactor suitable for solid-liquid contacting. The digestion may for example be conducted in a single or multiple vessels, with biomass solids either fully immersed in liquid digestive solvent, or contacted with solvent in a trickle bed or pile digestion mode. As a further example, the digestion step may occur in a continuous multizone contactor as described in U.S. Pat. No. 7,285,179 (Snekkenes et al., "Continuous Digester for Cellulose Pulp including Method and Recirculation System for such Digester"), which disclosure is hereby incorporated by reference in its entirety. Alternately, the digestion may occur in a fluidized bed or stirred contactor, with suspended solids. The digestion may be conducted batch wise, in the same vessel used for pre-wash, post wash, and/or subsequent reaction steps. The digestion may also be conducted in a counter-flow configuration as further described below.

The relative composition and concentration of the various carbohydrate components in the digested biomass stream affects the formation of undesirable by-products such as tars or heavy ends in the hydrocatalytic reaction. In particular, a low concentration of carbohydrates present as reducing sugars, or containing free aldehyde groups, in the digested biomass stream can minimize the formation of unwanted by-products. In preferred embodiments, it is desirable to have a concentration of no more than 5 wt %, based upon total liquid, of readily degradable carbohydrates or heavy end precursors in the treated biomass, while maintaining a total organic intermediates concentration, which can include the oxygenated intermediates (e.g., mono-oxygenates, diols, and/or polyols) derived from the carbohydrates, as high as possible, via use of concerted reaction or rapid recycle of the liquid between the digestion zone, and the hydrocatalytic reaction zone converting the solubilized carbohydrates to oxygenated intermediates.

Digestion of biomass occurs in the presence of water, to effect hydrolysis reactions as even the organic phase reactions need to preferably solubilize some water to effect digestion and "reforming" reactions. A minimum of about one weight percent water is preferred in the digester to effect these reactions. Water is in most cases present in the biomass feed. Hydrolysis of cellulose and hemicelluloses in the biomass feed results in solubilization of carbohydrate components into the digested biomass stream, which can be hydrocatalytically treated.

The digestion can be carried out in a suitable vessel, for example, a pressure vessel of carbon steel or stainless steel or similar alloy. The digestion zone can be carried out in the same vessel or in a separate vessel. The digestion can be conducted in continuous or batch mode. Suitable pressure vessels include, but are not limited to the "PANDIA™ Digester" (Voest-Alpine Industrienlagenbau GmbH, Linz, Austria), the "DEFIBRATOR Digester" (Sunds Defibrator AB Corporation, Stockholm, Sweden), M&D (Messing & Durkee) digester (Bauer Brothers Company, Springfield, Ohio, USA) and the KAMYR Digester (Andritz Inc., Glens Falls, N.Y., USA).

The hydrocatalytic treatment is conducted in the presence of molecular hydrogen, with a metal catalyst that is capable of activating molecular hydrogen ("molecular hydrogen activating catalyst") to participate in reactions such as reforming, hydrogenation, hydrogenolysis, hydrodeoxygenation, optionally hydrodesulfurization and hydrodenitrification. These reactions are important for conversion of unstable reactive intermediates derived from biomass feedstocks, to a more stable form via hydrogenation reactions, and also for generation of the desired mono-oxygenate intermediates desired for subsequent condensation and oligomerization to liquid biofuels. If molecular hydrogen or $H_2$ is not present, most catalysts which can activate $H_2$ can also form $H_2$ from soluble hydrocarbons and oxygenated hydrocarbons and water, via reforming reactions. Transition metal catalysts are most typically employed for activation of molecular hydrogen.

The hydrocatalytic treatment can comprise a combination of various different reaction pathways, including reforming, hydrogenolysis, hydrogenation, consecutive hydrogenation-hydrogenolysis, consecutive hydrogenolysis-hydrogenation, and combined hydrogenation-hydrogenolysis reactions, and any combination thereof. In one embodiment of the invention, the digested biomass containing carbohydrates may be converted into an stable hydroxyl intermediate comprising the corresponding alcohol derivative through a hydrogenolysis reaction in addition to an optional hydrogenation reaction in a suitable reaction vessel (such as hydrogenation reaction as described in co-pending U.S. Application Publication Nos. US20110154721 and US20110282115 which disclosures are hereby incorporated by reference in their entirety).

For hydrocatalytic treatment, one suitable method includes contacting the digested biomass stream containing carbohydrate or stable hydroxyl intermediate with hydrogen or hydrogen mixed with a suitable gas and a metal catalyst capable of activating molecular hydrogen to effect reforming, hydrogenation, hydrogenolysis, hydrodeoxygenation, and optionally hydrodesulfurization and hydrodenitrification reactions under conditions effective to form a reaction product comprising less reactive, smaller molecules or polyols and other oxygenated compounds. As used herein, the term "smaller molecules or polyols and other oxygenated compounds" includes any molecule that has a lower molecular weight, which can include a smaller number of carbon atoms or oxygen atoms than the starting carbohydrate. Less reactive refers to the conversion of aldehydic carbonyls, to alcohols. In an embodiment, the reaction products include smaller molecules that include polyols and alcohols.

One aspect of hydrogenolysis entails breaking of carbon-carbon bonds, where hydrogen is supplied to satisfy bonding requirements for the resulting smaller molecules, as shown for the example:

$$RC(H)_2\text{---}C(H)_2R' + H_2 \rightarrow RCH_3 + H_3CR'$$

where R and R' are any organic moieties.

In an embodiment, a carbohydrate (e.g., a 5 and/or 6 carbon carbohydrate molecule) can be converted to stable hydroxyl intermediates comprising propylene glycol, ethylene glycol, and glycerol using a hydrogenolysis reaction in the presence of a hydrogenolysis catalyst.

A second aspect of hydrogenolysis entails the breaking of —OH bonds such as:

$$RC(H)_2\text{---}OH + H_2 \rightarrow RCH_3 + H_2O$$

This reaction of breaking of —OH bonds is also called "hydrodeoxygenation" and may occur in parallel with C—C bond breaking hydrogenolysis. Selectivity for C—C vs. C—OH bond hydrogenolysis will vary with catalyst type and formulation.

The hydrogen used in the hydrocatalytic reactions can include external hydrogen, recycled hydrogen, in situ generated hydrogen, and any combination thereof. If in situ generated hydrogen is used, reforming reactions of carbohydrates to make hydrogen is preferred.

In one embodiment, the use of a hydrogenolysis reaction may produce less carbon dioxide as a byproduct, and a greater amount of polyols than a reaction that results in reforming of the carbohydrate reactants to generate hydrogen. For example, reforming can be illustrated by formation of isopropanol (i.e., IPA, or 2-propanol) from sorbitol:

$$C_6H_{14}O_6 + H_2O \rightarrow 4H_2 + 3CO_2 + C_3H_8O; \, dHR = -40 \text{ J/gmol} \quad (Eq. 1)$$

Alternately, in the presence of hydrogen, polyols and mono-oxygenates such as IPA can be formed by hydrogenolysis and hydrodeoxygenation reactions, where hydrogen is consumed rather than produced:

$$C_6H_{14}O_6 + 3H_2 \rightarrow 2H_2O + 2C_3H_8O_2; \, dHR = +81 \text{ J/gmol} \quad (Eq. 2)$$

$$C_6H_{14}O_6 + 5H_2 \rightarrow 4H_2O + 2C_3H_8O; \, dHR = -339 \text{ J/gmol} \quad (Eq. 3)$$

The conditions for which to carry out hydrocatalytic treatment will vary based on the type of biomass starting material and the desired products (e.g. gasoline or diesel). One of ordinary skill in the art, with the benefit of this disclosure, will recognize the appropriate conditions to use to carry out the reaction. In general, hydrogenation reactions can start as low a 60° C., with a typical range of 80-150° C., while the hydrogenolysis reaction can be conducted at temperatures in the range of 110° C. to 300° C., and preferably of 170° C. to 300° C., and most preferably of 180° C. to 290° C.

In an embodiment, the hydrogenolysis reaction is conducted under basic conditions, preferably at a pH of 8 to 13, and even more preferably at a pH of 10 to 12. In another embodiment, the hydrogenolysis reaction is conducted under neutral to mildly acidic conditions. In an embodiment, the hydrogenolysis reaction is conducted at pressures in a range between about 1 and 200 bar, and preferably in a range between 15 and 150 bar, and even more preferably between 35 bar and 100 bar.

The hydrocatalytic treatment catalyst or the molecular hydrogen activating catalyst may include a support material that has incorporated therein or is loaded with a metal component, which is or can be converted to a metal compound that has activity towards the catalytic reforming, hydrogenation, hydrogenolysis, and/or hydrodeoxygenation of soluble carbohydrates. The support material can comprise any suitable inorganic oxide material that is typically used to carry catalytically active metal components. Examples of possible useful inorganic oxide materials include alumina, silica, silica-alumina, magnesia, zirconia, boria, titania and mixtures of any two or more of such inorganic oxides. The preferred inorganic oxides for use in the formation of the support material are alumina, silica, silica-alumina and mixtures thereof. Most preferred, however, is alumina.

In the preparation of the hydrocatalytic treatment catalyst, the metal component of the catalyst composition may be incorporated into the support material by any suitable method or means that provides the support material that is loaded with an active metal precursor, thus, the composition includes the support material and a metal component. One method of incorporating the metal component into the support material, includes, for example, co-mulling the support material with the active metal or metal precursor to yield a co-mulled mixture of the two components. Or, another method includes the co-precipitation of the support material and metal component to form a co-precipitated mixture of the support material and metal component. Or, in a preferred method, the support material is impregnated with the metal component using any of the known impregnation methods such as incipient wetness to incorporate the metal component into the support material When using the impregnation method to incorporate the metal component into the support material, it is preferred for the support material to be formed into a shaped particle comprising an inorganic oxide material and thereafter loaded with an active metal precursor, preferably, by the impregnation of the shaped particle with an aqueous solution of a metal salt to give the support material containing a metal of a metal salt solution. To form the shaped particle, the inorganic oxide material, which preferably is in powder form, is mixed with water and, if desired or needed, a peptizing agent and/or a binder to form a mixture that can be shaped into an agglomerate. It is desirable for the mixture to be in the form of an extrudable paste suitable for extrusion into extrudate particles, which may be of various shapes such as cylinders, trilobes, etc. and nominal sizes such as 1/16", 1/8", 3/16", etc. The support material of the inventive composition, thus, preferably, is a shaped particle comprising an inorganic oxide material.

The calcined shaped particle can have a surface area (determined by the BET method employing $N_2$, ASTM test method D 3037) that is in the range of from about 50 $m^2/g$ to about 450 $m^2/g$, preferably from about 75 $m^2/g$ to about 400 $m^2/g$, and, most preferably, from about 100 $m^2/g$ to about 350 $m^2/g$. The mean pore diameter in angstroms (Å) of the calcined shaped particle is in the range of from about 50 to about 200, preferably, from about 70 to about 150, and, most preferably, from about 75 to about 125. The pore volume of the calcined shaped particle is in the range of from about 0.5 cc/g to about 1.1 cc/g, preferably, from about 0.6 cc/g to about 1.0 cc/g, and, most preferably, from about 0.7 to about 0.9 cc/g. Less than ten percent (10%) of the total pore volume of the calcined shaped particle is contained in the pores having a pore diameter greater than about 350 Å, preferably, less than about 7.5% of the total pore volume of the calcined shaped particle is contained in the pores having a pore diameter greater than about 350 Å, and, most preferably, less than about 5%.

The references herein to the pore size distribution and pore volume of the calcined shaped particle are to those properties as determined by mercury intrusion porosimetry, ASTM test method D 4284. The measurement of the pore size distribution of the calcined shaped particle is by any suitable measurement instrument using a contact angle of 140° with a mercury surface tension of 474 dyne/cm at 25° C.

In one embodiment, the calcined shaped particle is impregnated in one or more impregnation steps with a metal component using one or more aqueous solutions containing at least one metal salt wherein the metal compound of the metal salt solution is an active metal or active metal precursor. The metal elements are (a) molybdenum (Mo) and (b) cobalt (Co) and/or nickel (Ni). Phosphorous (P) can also be a desired metal component. For Co and Ni, the metal salts include metal acetates, formats, citrates, oxides, hydroxides, carbonates, nitrates, sulfates, and two or more thereof. The preferred metal salts are metal nitrates, for example, such as nitrates of nickel or cobalt, or both. For Mo, the metal salts include metal oxides or sulfides. Preferred are salts containing the Mo and ammonium ion, such as ammonium heptamolybdate and ammonium dimolybdate.

The concentration of the metal compounds in the impregnation solution is selected so as to provide the desired metal content in the final composition of the hydrocatalytic treatment catalyst taking into consideration the pore volume of the support material into which the aqueous solution is to be impregnated. Typically, the concentration of metal compound in the impregnation solution is in the range of from 0.01 to 100 moles per liter.

Cobalt, nickel, or combination thereof can be present in the support material having a metal component incorporated therein in an amount in the range of from about 0.5 wt. % to about 20 wt. %, preferably from about 1 wt. % to about 15 wt. %, and, most preferably, from about 2 wt. % to about 12 wt. %, based on metals components (b) and (c) as metal oxide form; and molybdenum can be present in the support material having a metal component incorporated therein in an amount in the range of from about 2 wt. % to about 50 wt. %, preferably from about 5 wt. % to about 40 wt. %, and, most preferably, from about 12 wt. % to about 30 wt. %, based on metals components (b) and (c) as metal oxide form. The above-referenced weight percents for the metal components are based on the dry support material and the metal component regardless of the actual form of the metal component.

The metal loaded catalyst may be sulfided prior to its loading into a reactor vessel or system for its use as hydrocatalytic treatment catalyst or may be sulfided, in situ, in a gas phase or liquid phase activation procedure. In one embodiment, the liquid soluble carbohydrate feedstock can be contacted with a sulfur-containing compound, which can be hydrogen sulfide or a compound that is decomposable into hydrogen sulfide, under the contacting conditions of the invention. Examples of such decomposable compounds include mercaptans, $CS_2$, thiophenes, dimethyl sulfide (DMS), dimethyl sulfoxide (DMSO), sodium hydrogen sulfate, and dimethyl disulfide (DMDS). Also, preferably, the sulfiding is accomplished by contacting the hydrogen treated composition, under suitable sulfurization treatment conditions, with a suitable feedsource that contains a concentration of a sulfur compound. The sulfur compound of the hydrocarbon feedstock can be an organic sulfur compound, particularly, one that is derived from the biomass feedstock or other sulfur containing amino-acids such as Cysteine.

Suitable sulfurization treatment conditions are those which provide for the conversion of the active metal components of the precursor hydrogenolysis catalyst to their sulfided form. Typically, the sulfiding temperature at which the precursor hydrogenolysis catalyst is contacted with the sulfur compound is in the range of from about 150° C. to about 450° C., preferably, from about 175° C. to about 425° C., and, most preferably, from about 200° C. to about 400° C.

When using a soluble carbohydrate feedstock that is to be treated using the catalyst to sulfide, the sulfurization conditions can be the same as the process conditions under which the hydrogenolysis is performed. The sulfiding pressure generally can be in the range of from about 1 bar to about 70 bar, preferably, from about 1.5 bar to about 55 bar, and, most preferably, from about 2 bar to about 35 bar. The resulting active catalyst typically has incorporated therein sulfur content in an amount in the range of from about 0.1 wt. % to about 40 wt. %, preferably from about 1 wt. % to about 30 wt. %, and, most preferably, from about 3 wt. % to about 24 wt. %, based on metals components (b) and (c) as metal oxide form.

In some embodiments, the hydrocatalytic treatment catalysts can be a heterogeneous catalyst capable of catalyzing a reaction between hydrogen and carbohydrate, oxygenated intermediate, or both to remove one or more oxygen atoms to produce alcohols and polyols to be fed to the condensation reactor. The hydrocatalytic treatment catalyst can generally include Cu, Re, Ni, Fe, Co, Ru, Pd, Rh, Pt, Os, Ir, Sn, and alloys or any combination thereof, either alone or with promoters such as W, Mo, Au, Ag, Cr, Zn, Mn, B, P, Bi, and alloys or any combination thereof. Other effective hydrocatalytic treatment catalyst materials include either supported nickel or ruthenium modified with rhenium. In some embodiments, the hydrocatalytic treatment catalyst also includes any one of the supports, depending on the desired functionality of the catalyst. The hydrocatalytic treatment catalysts may be prepared by methods known to those of ordinary skill in the art. In some embodiments the hydrocatalytic treatment catalyst includes a supported Group VIII metal catalyst and a metal sponge material (e.g., a sponge nickel catalyst). Raney nickel provides an example of an activated sponge nickel catalyst suitable for use in this invention. In some embodiments, the hydrocatalytic treatment in the invention is performed using a catalyst comprising a nickel-rhenium catalyst or a tungsten-modified nickel catalyst. One example of a suitable catalyst for the hydrocatalytic treatment of the invention is a carbon-supported nickel-rhenium catalyst.

In some embodiments, a suitable Raney nickel catalyst may be prepared by treating an alloy of approximately equal amounts by weight of nickel and aluminum with an aqueous alkali solution, e.g., containing about 25 weight % of sodium hydroxide. The aluminum is selectively dissolved by the aqueous alkali solution resulting in a sponge shaped material comprising mostly nickel with minor amounts of aluminum. The initial alloy includes promoter metals (e.g., molybdenum or chromium) in the amount such that 1 to 2 weight % remains in the formed sponge nickel catalyst. In another embodiment, the hydrocatalytic treatment catalyst is prepared using a solution of ruthenium (III) nitrosylnitrate, ruthenium (III) chloride in water to impregnate a suitable support material. The solution is then dried to form a solid having a water content of less than 1% by weight. The solid is then reduced at atmospheric pressure in a hydrogen stream at 300° C. (uncalcined) or 400° C. (calcined) in a rotary ball furnace for 4 hours. After cooling and rendering the catalyst inert with nitrogen, 5% by volume of oxygen in nitrogen is passed over the catalyst for 2 hours.

In certain embodiments, the hydrocatalytic treatment catalyst may include a catalyst support. The catalyst support stabilizes and supports the catalyst. The type of catalyst support used depends on the chosen catalyst and the reaction conditions. Suitable supports for the invention include, but are not limited to, carbon, silica, silica-alumina, zirconia, titania, ceria, vanadia, nitride, boron nitride, heteropolyacids, hydroxyapatite, zinc oxide, chromia, zeolites, carbon nanotubes, carbon fullerene and any combination thereof.

In some embodiments, the oxygenated hydrocarbon molecules and hydrocarbon molecules in the hydrocatalytically treated mixtures (intermediates), can be converted into higher hydrocarbons through a processing reaction. In an embodiment, the processing reaction may comprise a condensation reaction to produce a fuel blend. In an embodiment, the higher hydrocarbons may be part of a fuel blend for use as a transportation fuel. In such an embodiment, condensation of the oxygenated intermediates occurs in the presence of a catalyst capable of forming higher hydrocarbons. While not intending to be limited by theory, it is believed that the production of higher hydrocarbons proceeds through a stepwise addition reaction including the formation of carbon-carbon bond. The resulting reaction products include any number of compounds, as described in more detail below.

In some embodiments, an outlet stream containing at least a portion of the intermediates can pass to a processing reaction or processing reactions. Suitable processing reactions may comprise a variety of catalysts for condensing one or more intermediates to higher hydrocarbons, defined as hydrocarbons containing more carbons than the precursors. The higher hydrocarbons may comprise a fuel product. The fuel products produced by the processing reactions represent the product stream from the overall process at higher hydrocarbon stream. In an embodiment, the oxygen to carbon ratio of the higher hydrocarbons produced through the processing reactions is less than 0.5, alternatively less than 0.4, or preferably less than 0.3.

The oxygenated hydrocarbon molecules (or "intermediates or oxygenated intermediates") can be processed to produce a fuel blend in one or more processing reactions. In an embodiment, a condensation reaction can be used along with other reactions to generate a fuel blend and may be catalyzed by a catalyst comprising acid or basic functional sites, or both. In general, without being limited to any particular theory, it is believed that the basic condensation reactions generally consist of a series of steps involving: (1) an optional dehydrogenation reaction; (2) an optional dehydration reaction that may be acid catalyzed; (3) an aldol condensation reaction; (4) an optional ketonization reaction; (5) an optional furanic ring opening reaction; (6) hydrogenation of the resulting condensation products to form a C4+ hydrocarbon; and (7) any combination thereof. Acid catalyzed condensations may similarly entail optional hydrogenation or dehydrogenation reactions, dehydration, and oligomerization reactions. Additional polishing reactions may also be used to conform the product to a specific fuel standard, including reactions conducted in the presence of hydrogen and a hydrogenation catalyst to remove functional groups from final fuel product. A catalyst comprising a basic functional site, both an acid and a basic functional site, and optionally comprising a metal function, may be used to effect the condensation reaction.

In an embodiment, the aldol condensation reaction may be used to produce a fuel blend meeting the requirements for a diesel fuel or jet fuel. Traditional diesel fuels are petroleum distillates rich in paraffinic hydrocarbons. They have boiling ranges as broad as 187° C. to 417° C., which are suitable for combustion in a compression ignition engine, such as a diesel engine vehicle. The American Society of Testing and Materials (ASTM) establishes the grade of diesel according to the boiling range, along with allowable ranges of other fuel properties, such as cetane number, cloud point, flash point, viscosity, aniline point, sulfur content, water content, ash content, copper strip corrosion, and carbon residue. Thus, any fuel blend meeting ASTM D975 can be defined as diesel fuel.

The present invention also provides methods to produce jet fuel. Jet fuel is clear to straw colored. The most common fuel is an unleaded/paraffin oil-based fuel classified as Aeroplane A-1, which is produced to an internationally standardized set of specifications. Jet fuel is a mixture of a large number of different hydrocarbons, possibly as many as a thousand or more. The range of their sizes (molecular weights or carbon numbers) is restricted by the requirements for the product, for example, freezing point or smoke point. Kerosene-type Airplane fuel (including Jet A and Jet A-1) has a carbon number distribution between about C8 and C16. Wide-cut or naphtha-type Airplane fuel (including Jet B) typically has a carbon number distribution between about C5 and C15. A fuel blend meeting ASTM D1655 can be defined as jet fuel.

In certain embodiments, both Airplanes (Jet A and Jet B) contain a number of additives. Useful additives include, but are not limited to, antioxidants, antistatic agents, corrosion inhibitors, and fuel system icing inhibitor (FSII) agents. Antioxidants prevent gumming and usually, are based on alkylated phenols, for example, AO-30, AO-31, or AO-37. Antistatic agents dissipate static electricity and prevent sparking. Stadis 450 with dinonylnaphthylsulfonic acid (DINNSA) as the active ingredient, is an example. Corrosion inhibitors, e.g., DCI-4A are used for civilian and military fuels and DCI-6A is used for military fuels. FSII agents, include, e.g., Di-EGME.

In an embodiment, the intermediates may comprise a carbonyl-containing compound that can take part in a base catalyzed condensation reaction. In some embodiments, an optional dehydrogenation reaction may be used to increase the amount of carbonyl-containing compounds in the oxygenated hydrocatalytically treated mixture to be used as a feed to the condensation reaction. In these embodiments, the intermediates and/or a portion of the biomass feedstock stream can be dehydrogenated in the presence of a catalyst.

In an embodiment, a dehydrogenation catalyst may be preferred for an oxygenated hydrocatalytically treated mixture comprising alcohols, diols, and triols. In general, alcohols cannot participate in aldol condensation directly. The hydroxyl group or groups present can be converted into carbonyls (e.g., aldehydes, ketones, etc.) in order to participate in an aldol condensation reaction. A dehydrogenation catalyst may be included to effect dehydrogenation of any alcohols, diols, or polyols present to form ketones and aldehydes. The dehydration catalyst is typically formed from the same metals as used for hydrogenolysis, hydrogenolysis, or aqueous phase reforming, which catalysts are described in more detail above. Dehydrogenation yields are enhanced by the removal or consumption of hydrogen as it forms during the reaction. The dehydrogenation step may be carried out as a separate reaction step before an aldol condensation reaction, or the dehydrogenation reaction may be carried out in concert with the aldol condensation reaction. For concerted dehydrogenation and aldol condensation, the dehydrogenation and aldol condensation functions can be on the same catalyst. For example, a metal hydrogenation/dehydrogenation functionality may be present on catalyst comprising a basic functionality.

The dehydrogenation reaction may result in the production of a carbonyl-containing compound. Suitable carbonyl-containing compounds include, but are not limited to, any compound comprising a carbonyl functional group that can form carbanion species or can react in a condensation reaction with a carbanion species, where "carbonyl" is defined as a carbon atom doubly-bonded to oxygen. In an embodiment, a carbonyl-containing compound can include, but is not limited to, ketones, aldehydes, furfurals, hydroxy carboxylic acids, and, carboxylic acids. The ketones may include, without limitation, hydroxyketones, cyclic ketones, diketones, acetone, propanone, 2-oxopropanal, butanone, butane-2,3-dione, 3-hydroxybutane-2-one, pentanone, cyclopentanone, pentane-2,3-dione, pentane-2,4-dione, hexanone, cyclohexanone, 2-methyl-cyclopentanone, heptanone, octanone, nonanone, decanone, undecanone, dodecanone, methylglyoxal, butanedione, pentanedione, diketohexane, dihydroxyacetone, and isomers thereof. The aldehydes may include, without limitation, hydroxyaldehydes, acetaldehyde, glyceraldehyde, propionaldehyde, butyraldehyde, pentanal, hexanal, heptanal, octanal, nonal, decanal, undecanal, dodecanal, and isomers thereof. The carboxylic acids may include, without limitation, formic acid, acetic acid, propionic acid, butanoic acid, pentanoic acid, hexanoic acid, heptanoic acid, isomers and derivatives thereof, including hydroxylated derivatives, such as 2-hydroxybutanoic acid and lactic acid. Furfurals include, without limitation, hydroxymethylfurfural, 5-hydroxymethyl-2(5H)-furanone, dihydro-5-(hydroxymethyl)-2(3H)-furanone, tetrahydro-2-furoic acid, dihydro-5-(hydroxymethyl)-2(3H)-furanone, tetrahydrofurfuryl alcohol, 1-(2-furyl)ethanol, hydroxymethyltetrahydrofurfural, and isomers thereof. In an embodiment, the dehydrogenation reaction results in the production of a carbonyl-containing compound that is combined with the intermediates to become a part of the intermediates fed to the condensation reaction.

In an embodiment, an acid catalyst may be used to optionally dehydrate at least a portion of the oxygenated hydrocatalytically treated mixture. Suitable acid catalysts for use in the dehydration reaction include, but are not limited to, mineral acids (e.g., HCl, $H_2SO_4$), solid acids (e.g., zeolites, ion-exchange resins) and acid salts (e.g., $LaCl_3$). Additional acid catalysts may include, without limitation, zeolites, carbides, nitrides, zirconia, alumina, silica, aluminosilicates, phosphates, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and any combination thereof. In some embodiments, the dehydration catalyst can also include a modifier. Suitable modifiers include La, Y, Sc, P, B, Bi, Li, Na, K, Rb, Cs, Mg, Ca, Sr, Ba, and any combination thereof. The modifiers may be useful, inter alia, to carry out a concerted hydrogenation/dehydrogenation reaction with the dehydration reaction. In some embodiments, the dehydration catalyst can also include a metal. Suitable metals include Cu, Ag, Au, Pt, Ni, Fe, Co, Ru, Zn, Cd, Ga, In, Rh, Pd, Ir, Re, Mn, Cr, Mo, W, Sn, Os, alloys, and any combination thereof. The dehydration catalyst may be self supporting, supported on an inert support or resin, or it may be dissolved in solution.

In some embodiments, the dehydration reaction occurs in the vapor phase. In other embodiments, the dehydration reaction occurs in the liquid phase. For liquid phase dehydration reactions, an aqueous solution may be used to carry out the reaction. In an embodiment, other solvents in addition to water, are used to form the aqueous solution. For example, water soluble organic solvents may be present. Suitable solvents can include, but are not limited to, hydroxymethylfurfural (HMF), dimethylsulfoxide (DMSO), 1-methyl-n-pyrollidone (NMP), and any combination thereof. Other suitable aprotic solvents may also be used alone or in combination with any of these solvents.

In an embodiment, the processing reactions may comprise an optional ketonization reaction. A ketonization reaction may increase the number of ketone functional groups within at least a portion of the oxygenated hydrocatalytically treated mixture. For example, an alcohol or other hydroxyl functional group can be converted into a ketone in a ketonization reaction. Ketonization may be carried out in the presence of a base catalyst. Any of the base catalysts described above as the basic component of the aldol condensation reaction can be used to effect a ketonization reaction. Suitable reaction conditions are known to one of ordinary skill in the art and generally correspond to the reaction conditions listed above with respect to the aldol condensation reaction. The ketonization reaction may be carried out as a separate reaction step, or it may be carried out in concert with the aldol condensation reaction. The inclusion of a basic functional site on the aldol condensation catalyst may result in concerted ketonization and aldol condensation reactions.

In an embodiment, the processing reactions may comprise an optional furanic ring opening reaction. A furanic ring opening reaction may result in the conversion of at least a portion of any intermediates comprising a furanic ring into compounds that are more reactive in an aldol condensation reaction. A furanic ring opening reaction may be carried out in the presence of an acidic catalyst. Any of the acid catalysts described above as the acid component of the aldol condensation reaction can be used to effect a furanic ring opening reaction. Suitable reaction conditions are known to one of ordinary skill in the art and generally correspond to the reaction conditions listed above with respect to the aldol condensation reaction. The furanic ring opening reaction may be carried out as a separate reaction step, or it may be carried out in concert with the aldol condensation reaction. The inclusion of an acid functional site on the aldol condensation catalyst may result in a concerted furanic ring opening reaction and aldol condensation reactions. Such an embodiment may be advantageous as any furanic rings can be opened in the presence of an acid functionality and reacted in an aldol condensation reaction using a base functionality. Such a concerted reaction scheme may allow for the production of a greater amount of higher hydrocarbons to be formed for a given oxygenated intermediate feed.

In an embodiment, production of a C4+ compound occurs by condensation, which may include aldol-condensation, of the intermediates in the presence of a condensation catalyst. Aldol-condensation generally involves the carbon-carbon coupling between two compounds, at least one of which may contain a carbonyl group, to form a larger organic molecule. For example, acetone may react with hydroxymethylfurfural to form a C9 species, which may subsequently react with another hydroxymethylfurfural molecule to form a C15 species. The reaction is usually carried out in the presence of a condensation catalyst. The condensation reaction may be carried out in the vapor or liquid phase. In an embodiment, the reaction may take place at a temperature in the range of from about 7° C. to about 377° C., depending on the reactivity of the carbonyl group.

The condensation catalyst will generally be a catalyst capable of forming longer chain compounds by linking two molecules through a new carbon-carbon bond, such as a basic catalyst, a multi-functional catalyst having both acid and base functionality, or either type of catalyst also comprising an optional metal functionality. In an embodiment, the multi-functional catalyst will be a catalyst having both a strong acid and a strong base functionality. In an embodiment, aldol catalysts can comprise Li, Na, K, Cs, B, Rb, Mg, Ca, Sr, Si, Ba, Al, Zn, Ce, La, Y, Sc, Y, Zr, Ti, hydrotalcite, zinc-aluminate, phosphate, base-treated aluminosilicate zeolite, a basic resin, basic nitride, alloys or any combination thereof. In an embodiment, the base catalyst can also comprise an oxide of Ti, Zr, V, Nb, Ta, Mo, Cr, W, Mn, Re, Al, Ga, In, Co, Ni, Si, Cu, Zn, Sn, Cd, Mg, P, Fe, or any combination thereof. In an embodiment, the condensation catalyst comprises mixed-oxide base catalysts. Suitable mixed-oxide base catalysts can comprise a combination of magnesium, zirconium, and oxygen, which may comprise, without limitation: Si—Mg—O, Mg—Ti—O, Y—Mg—O, Y—Zr—O, Ti—Zr—O, Ce—Zr—O, Ce—Mg—O, Ca—Zr—O, La—Zr—O, B—Zr—O, La—Ti—O, B—Ti—O, and any combinations thereof. Different atomic ratios of Mg/Zr or the combinations of various other elements constituting the mixed oxide catalyst may be used ranging from about 0.01 to about 50. In an embodiment, the condensation catalyst further includes a metal or alloys comprising metals, such as Cu, Ag, Au, Pt, Ni, Fe, Co, Ru, Zn, Cd, Ga, In, Rh, Pd, Ir, Re, Mn, Cr, Mo, W, Sn, Bi, Pb, Os, alloys and combinations thereof. Such metals may be preferred when a dehydrogenation reaction is to be carried out in concert with the aldol condensation reaction. In an embodiment, preferred Group IA materials include Li, Na, K, Cs and Rb. In an embodiment, preferred Group IIA materials include Mg, Ca, Sr and Ba. In an embodiment, Group IIB materials include Zn and Cd. In an embodiment, Group IIIB materials include Y and La. Basic resins include resins that exhibit basic functionality. The base catalyst may be self-supporting or adhered to any one of the supports further described below, including supports containing carbon, silica, alumina, zirconia, titania, vanadia, ceria, nitride, boron nitride, heteropolyacids, alloys and mixtures thereof.

In one embodiment, the condensation catalyst is derived from the combination of MgO and Al2O3 to form a hydrotalcite material. Another preferred material contains ZnO and Al2O3 in the form of a zinc aluminate spinel. Yet another preferred material is a combination of ZnO, Al2O3, and CuO. Each of these materials may also contain an additional metal function provided by a Group VIIIB metal, such as Pd or Pt. Such metals may be preferred when a dehydrogenation reaction is to be carried out in concert with the aldol condensation reaction. In one embodiment, the base catalyst is a metal oxide containing Cu, Ni, Zn, V, Zr, or mixtures thereof. In another embodiment, the base catalyst is a zinc aluminate metal containing Pt, Pd Cu, Ni, or mixtures thereof.

Preferred loading of the primary metal in the condensation catalyst is in the range of 0.10 wt % to 25 wt %, with weight percentages of 0.10% and 0.05% increments between, such as 1.00%, 1.10%, 1.15%, 2.00%, 2.50%, 5.00%, 10.00%, 12.50%, 15.00% and 20.00%. The preferred atomic ratio of the second metal, if any, is in the range of 0.25-to-1 to 10-to-1, including ratios there between, such as 0.50, 1.00, 2.50, 5.00, and 7.50-to-1.

In some embodiments, the base catalyzed condensation reaction is performed using a condensation catalyst with both an acid and base functionality. The acid-aldol condensation catalyst may comprise hydrotalcite, zinc-aluminate, phosphate, Li, Na, K, Cs, B, Rb, Mg, Si, Ca, Sr, Ba, Al, Ce, La, Sc, Y, Zr, Ti, Zn, Cr, or any combination thereof. In further embodiments, the acid-base catalyst may also include one or more oxides from the group of Ti, Zr, V, Nb, Ta, Mo, Cr, W, Mn, Re, Al, Ga, In, Fe, Co, Ir, Ni, Si, Cu, Zn, Sn, Cd, P, and combinations thereof. In an embodiment, the acid-base catalyst includes a metal functionality provided by Cu, Ag, Au, Pt, Ni, Fe, Co, Ru, Zn, Cd, Ga, In, Rh, Pd, Ir, Re, Mn, Cr, Mo, W, Sn, Os, alloys or combinations thereof. In one embodiment, the catalyst further includes Zn, Cd or phosphate. In one embodiment, the condensation catalyst is a metal oxide containing Pd, Pt, Cu or Ni, and even more preferably an aluminate or zirconium metal oxide containing Mg and Cu, Pt, Pd or Ni. The acid-base catalyst may also include a hydroxyapatite (HAP) combined with any one or more of the above metals. The acid-base catalyst may be self-supporting or adhered to any one of the supports further described below, including supports containing carbon, silica, alumina, zirconia, titania, vanadia, ceria, nitride, boron nitride, heteropolyacids, alloys and mixtures thereof.

In an embodiment, the condensation catalyst may also include zeolites and other microporous supports that contain Group IA compounds, such as Li, NA, K, Cs and Rb. Preferably, the Group IA material is present in an amount less than that required to neutralize the acidic nature of the support. A metal function may also be provided by the addition of group VIIIB metals, or Cu, Ga, In, Zn or Sn. In one embodiment, the condensation catalyst is derived from the combination of MgO and Al2O3 to form a hydrotalcite material. Another preferred material contains a combination of MgO and ZrO2, or a combination of ZnO and Al2O3. Each of these materials may also contain an additional metal function provided by copper or a Group VIIIB metal, such as Ni, Pd, Pt, or combinations of the foregoing.

If a Group IIB, VIIB, VIIB, VIIIB, IIA or IVA metal is included in the condensation catalyst, the loading of the metal is in the range of 0.10 wt % to 10 wt %, with weight percentages of 0.10% and 0.05% increments between, such as 1.00%, 1.10%, 1.15%, 2.00%, 2.50%, 5.00% and 7.50%, etc. If a second metal is included, the preferred atomic ratio of the second metal is in the range of 0.25-to-1 to 5-to-1, including ratios there between, such as 0.50, 1.00, 2.50 and 5.00-to-1.

The condensation catalyst may be self-supporting (i.e., the catalyst does not need another material to serve as a support), or may require a separate support suitable for suspending the catalyst in the reactant stream. One exemplary support is silica, especially silica having a high surface area (greater than 100 square meters per gram), obtained by sol-gel synthesis, precipitation, or fuming. In other embodiments, particularly when the condensation catalyst is a powder, the catalyst system may include a binder to assist in forming the catalyst into a desirable catalyst shape. Applicable forming processes include extrusion, pelletization, oil dropping, or other known processes. Zinc oxide, alumina, and a peptizing agent may also be mixed together and extruded to produce a formed material. After drying, this material is calcined at a temperature appropriate for formation of the catalytically active phase, which usually requires temperatures in excess of 452° C. Other catalyst supports as known to those of ordinary skill in the art may also be used.

In some embodiments, a dehydration catalyst, a dehydrogenation catalyst, and the condensation catalyst can be present in the same reactor as the reaction conditions overlap to some degree. In these embodiments, a dehydration reaction and/or a dehydrogenation reaction may occur substantially simultaneously with the condensation reaction. In some embodiments, a catalyst may comprise active sites for a dehydration reaction and/or a dehydrogenation reaction in addition to a condensation reaction. For example, a catalyst may comprise active metals for a dehydration reaction and/or a dehydrogenation reaction along with a condensation reaction at separate sites on the catalyst or as alloys. Suitable active elements can comprise any of those listed above with respect to the dehydration catalyst, dehydrogenation catalyst, and the condensation catalyst. Alternately, a physical mixture of dehydration, dehydrogenation, and condensation catalysts could be employed. While not intending to be limited by theory, it is believed that using a condensation catalyst comprising a metal and/or an acid functionality may assist in pushing the equilibrium limited aldol condensation reaction towards completion. Advantageously, this can be used to effect multiple condensation reactions with dehydration and/or dehydrogenation of intermediates, in order to form (via condensation, dehydration, and/or dehydrogenation) higher molecular weight oligomers as desired to produce jet or diesel fuel.

The specific C4+ compounds produced in the condensation reaction will depend on various factors, including, without limitation, the type of intermediates in the reactant stream, condensation temperature, condensation pressure, the reactivity of the catalyst, and the flow rate of the reactant stream as it affects the space velocity, GHSV and WHSV. Preferably, the reactant stream is contacted with the condensation catalyst at a WHSV that is appropriate to produce the desired hydrocarbon products. The WHSV is preferably at least about 0.1 grams of intermediates in the reactant stream per hour, more preferably the WHSV is between about 0.1 to 40.0 g/g hr, including a WHSV of about 1, 2, 3, 4, 5, 6, 7, 8, 9, 10, 11, 12, 13, 14, 15, 20, 25, 30, 35 g/g hr, and increments between.

In general, the condensation reaction should be carried out at a temperature at which the thermodynamics of the proposed reaction are favorable. For condensed phase liquid reactions, the pressure within the reactor must be sufficient to maintain at least a portion of the reactants in the condensed liquid phase at the reactor inlet. For vapor phase reactions, the reaction should be carried out at a temperature where the vapor pressure of the oxygenates is at least about 10 kPa, and the thermodynamics of the reaction are favorable. The condensation temperature will vary depending upon the specific intermediates used, but is generally in the range of from about 77° C. to 502° C. for reactions taking place in the vapor phase, and more preferably from about 127° C. to 452° C. For liquid phase reactions, the condensation temperature may be from about 7° C. to 477° C., and the condensation pressure from about 0.1 kPa to 10,000 kPa. Preferably, the condensation temperature is between about 17° C. and 302° C., or between about 17° C. and 252° C. for difficult substrates.

Varying the factors above as well as others, will generally result in a modification to the specific composition and yields of the C4+ compounds. For example, varying the temperature and/or pressure of the reactor system, or the particular catalyst formulations, may result in the production of C4+ alcohols and/or ketones instead of C4+ hydrocarbons. The C4+ hydrocarbon product may also contain a variety of olefins, and alkanes of various sizes (typically branched alkanes). Depending upon the condensation catalyst used, the hydrocarbon product may also include aromatic and cyclic hydrocarbon compounds. The C4+ hydrocarbon product may also contain undesirably high levels of olefins, which may lead to coking or deposits in combustion engines, or other undesirable hydrocarbon products. In such event, the hydrocarbon molecules produced may be optionally hydrogenated to reduce the ketones to alcohols and hydrocarbons, while the alcohols and unsaturated hydrocarbon may be reduced to alkanes, thereby forming a more desirable hydrocarbon product having low levels of olefins, aromatics or alcohols.

The condensation reactions may be carried out in any reactor of suitable design, including continuous-flow, batch, semi-batch or multi-system reactors, without limitation as to design, size, geometry, flow rates, etc. The reactor system may also use a fluidized catalytic bed system, a swing bed system, fixed bed system, a moving bed system, or a combination of the above. In some embodiments, bi-phasic (e.g., liquid-liquid) and tri-phasic (e.g., liquid-liquid-solid) reactors may be used to carry out the condensation reactions.

In a continuous flow system, the reactor system can include an optional dehydrogenation bed adapted to produce dehydrogenated intermediates, an optional dehydration bed adapted to produce dehydrated intermediates, and a condensation bed to produce C4+ compounds from the intermediates. The dehydrogenation bed is configured to receive the reactant stream and produce the desired intermediates, which may have an increase in the amount of carbonyl-containing compounds. The de-hydration bed is configured to receive the reactant stream and produce the desired intermediates. The condensation bed is configured to receive the intermediates for contact with the condensation catalyst and production of the desired C4+ compounds. For systems with one or more finishing steps, an additional reaction bed for conducting the finishing process or processes may be included after the condensation bed.

In an embodiment, the optional dehydration reaction, the optional dehydrogenation reaction, the optional ketonization reaction, the optional ring opening reaction, and the condensation reaction catalyst beds may be positioned within the same reactor vessel or in separate reactor vessels in fluid communication with each other. Each reactor vessel preferably includes an outlet adapted to remove the product stream from the reactor vessel. For systems with one or more finishing steps, the finishing reaction bed or beds may be within the same reactor vessel along with the condensation bed or in a separate reactor vessel in fluid communication with the reactor vessel having the condensation bed.

In an embodiment, the reactor system also includes additional outlets to allow for the removal of portions of the reactant stream to further advance or direct the reaction to the desired reaction products, and to allow for the collection and recycling of reaction byproducts for use in other portions of the system. In an embodiment, the reactor system also includes additional inlets to allow for the introduction of supplemental materials to further advance or direct the reaction to the desired reaction products, and to allow for the recycling of reaction byproducts for use in other reactions.

In an embodiment, the reactor system also includes elements which allow for the separation of the reactant stream into different components which may find use in different reaction schemes or to simply promote the desired reactions. For instance, a separator unit, such as a phase separator, extractor, purifier or distillation column, may be installed prior to the condensation step to remove water from the reactant stream for purposes of advancing the condensation reaction to favor the production of higher hydrocarbons. In an embodiment, a separation unit is installed to remove specific intermediates to allow for the production of a desired product stream containing hydrocarbons within a particular carbon number range, or for use as end products or in other systems or processes.

The condensation reaction can produce a broad range of compounds with carbon numbers ranging from C4 to C30 or greater. Exemplary compounds include, but are not limited to, C4+ alkanes, C4+ alkenes, C5+ cycloalkanes, C5+ cycloalkenes, aryls, fused aryls, C4+ alcohols, C4+ ketones, and mixtures thereof. The C4+ alkanes and C4+ alkenes may range from 4 to 30 carbon atoms (C4-C30 alkanes and C4-C30 alkenes) and may be branched or straight chained alkanes or alkenes. The C4+ alkanes and C4+ alkenes may also include fractions of C7-C14, C12-C24 alkanes and alkenes, respectively, with the C7-C14 fraction directed to jet fuel blend, and the C12-C24 fraction directed to a diesel fuel blend and other industrial applications. Examples of various C4+ alkanes and C4+ alkenes include, without limitation, butane, butene, pentane, pentene, 2-methylbutane, hexane, hexene, 2-methylpentane, 3-methylpentane, 2,2-dimethylbutane, 2,3-dimethylbutane, heptane, heptene, octane, octene, 2,2,4,-trimethylpentane, 2,3-dimethyl hexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, hexadecane, hexadecene, heptyldecane, heptyldecene, octyldecane, octyldecene, nonyldecane, nonyldecene, eicosane, eicosene, uneicosane, uneicosene, doeicosane, doeicosene, trieicosane, trieicosene, tetraeicosane, tetraeicosene, and isomers thereof.

The C5+ cycloalkanes and C5+ cycloalkenes have from 5 to 30 carbon atoms and may be unsubstituted, mono-substituted or multi-substituted. In the case of mono-substituted and multi-substituted compounds, the substituted group may include a branched C3+ alkyl, a straight chain C1+ alkyl, a branched C3+ alkylene, a straight chain C1+ alkylene, a straight chain C2+ alkylene, a phenyl or a combination thereof. In one embodiment, at least one of the substituted groups include a branched C3-C12 alkyl, a straight chain C1-C12 alkyl, a branched C3-C12 alkylene, a straight chain C1-C12 alkylene, a straight chain C2-C12 alkylene, a phenyl or a combination thereof. In yet another embodiment, at least one of the substituted groups includes a branched C3-C4 alkyl, a straight chain C1-C4 alkyl, a branched C3-C4 alkylene, a straight chain C1-C4 alkylene, a straight chain C2-C4 alkylene, a phenyl, or any combination thereof. Examples of desirable C5+ cycloalkanes and C5+ cycloalkenes include, without limitation, cyclopentane, cyclopentene, cyclohexane, cyclohexene, methyl-cyclopentane, methyl-cyclopentene, ethyl-cyclopentane, ethyl-cyclopentene, ethyl-cyclohexane, ethyl-cyclohexene, and isomers thereof.

Aryls will generally consist of an aromatic hydrocarbon in either an unsubstituted (phenyl), mono-substituted or multi-substituted form. In the case of mono-substituted and multi-substituted compounds, the substituted group may include a branched C3+ alkyl, a straight chain C1+ alkyl, a branched C3+ alkylene, a straight chain C2+ alkylene, a phenyl or a combination thereof. In one embodiment, at least one of the substituted groups includes a branched C3-C12 alkyl, a straight chain C1-C12 alkyl, a branched C3-C12 alkylene, a straight chain C2-C12 alkylene, a phenyl, or any combination thereof. In yet another embodiment, at least one of the substituted groups includes a branched C3-C4 alkyl, a straight chain C1-C4 alkyl, a branched C3-C4 alkylene, straight chain C2-C4 alkylene, a phenyl, or any combination thereof. Examples of various aryls include, without limitation, benzene, toluene, xylene (dimethylbenzene), ethyl benzene, para xylene, meta xylene, ortho xylene, C9 aromatics.

Fused aryls will generally consist of bicyclic and polycyclic aromatic hydrocarbons, in either an unsubstituted, mono-substituted or multi-substituted form. In the case of mono-substituted and multi-substituted compounds, the substituted group may include a branched C3+ alkyl, a straight chain C1+ alkyl, a branched C3+ alkylene, a straight chain C2+ alkylene, a phenyl or a combination thereof. In another embodiment, at least one of the substituted groups includes a branched C3-C4 alkyl, a straight chain C1-C4 alkyl, a branched C3-C4 alkylene, a straight chain C2-C4 alkylene, a phenyl, or any combination thereof. Examples of various fused aryls include, without limitation, naphthalene, anthracene, tetrahydronaphthalene, and decahydronaphthalene, indane, indene, and isomers thereof.

The moderate fractions, such as C7-C14, may be separated for jet fuel, while heavier fractions, (e.g., C12-C24), may be separated for diesel use. The heaviest fractions may be used as lubricants or cracked to produce additional gasoline and/or diesel fractions. The C4+ compounds may also find use as industrial chemicals, whether as an intermediate or an end product. For example, the aryls toluene, xylene, ethyl benzene, para xylene, meta xylene, ortho xylene may find use as chemical intermediates for the production of plastics and other products. Meanwhile, the C9 aromatics and fused aryls, such as naphthalene, anthracene, tetrahydronaphthalene, and decahydronaphthalene, may find use as solvents in industrial processes.

In an embodiment, additional processes are used to treat the fuel blend to remove certain components or further conform the fuel blend to a diesel or jet fuel standard. Suitable techniques include hydrotreating to reduce the amount of or remove any remaining oxygen, sulfur, or nitrogen in the fuel blend. The conditions for hydrotreating a hydrocarbon stream are known to one of ordinary skill in the art.

In an embodiment, hydrogenation is carried out in place of or after the hydrotreating process to saturate at least some olefinic bonds. In some embodiments, a hydrogenation reaction may be carried out in concert with the aldol condensation reaction by including a metal functional group with the aldol condensation catalyst. Such hydrogenation may be performed to conform the fuel blend to a specific fuel standard (e.g., a diesel fuel standard or a jet fuel standard). The hydrogenation of the fuel blend stream can be carried out according to known procedures, either with the continuous or batch method. The hydrogenation reaction may be used to remove a remaining carbonyl group or hydroxyl group. In such event, any one of the hydrogenation catalysts described above may be used. Such catalysts may include any one or more of the following metals, Cu, Ni, Fe, Co, Ru, Pd, Rh, Pt, Ir, Os, alloys or combinations thereof, alone or with promoters such as Au, Ag, Cr, Zn, Mn, Sn, Cu, Bi, and alloys thereof, may be used in various loadings ranging from about 0.01 wt % to about 20 wt % on a support as described above. In general, the finishing step is carried out at finishing temperatures of between about 80° C. to 250° C., and finishing pressures in the range of about 700 kPa to 15,000 kPa. In one embodiment, the finishing step is conducted in the vapor phase or liquid phase, and uses, external $H_2$, recycled $H_2$, or combinations thereof, as necessary.

In an embodiment, isomerization is used to treat the fuel blend to introduce a desired degree of branching or other shape selectivity to at least some components in the fuel blend. It may be useful to remove any impurities before the hydrocarbons are contacted with the isomerization catalyst.

The isomerization step comprises an optional stripping step, wherein the fuel blend from the oligomerization reaction may be purified by stripping with water vapor or a suitable gas such as light hydrocarbon, nitrogen or hydrogen. The optional stripping step is carried out in a counter-current manner in a unit upstream of the isomerization catalyst, wherein the gas and liquid are contacted with each other, or before the actual isomerization reactor in a separate stripping unit utilizing counter-current principle.

After the optional stripping step the fuel blend can be passed to a reactive isomerization unit comprising one or several catalyst bed(s). The catalyst beds of the isomerization step may operate either in co-current or counter-current manner. In the isomerization step, the pressure may vary from 2000 kPa to 15,000 kPa, preferably in the range of 2000 kPa to 10,000 kPa, the temperature being between 197° C. and 502° C., preferably between 302° C. and 402° C. In the isomerization step, any isomerization catalysts known in the art may be used. Suitable isomerization catalysts can contain molecular sieve and/or a metal from Group VII and/or a carrier. In an embodiment, the isomerization catalyst contains SAPO-11 or SAPO41 or ZSM-22 or ZSM-23 or ferrierite and Pt, Pd or Ni and Al2O3 or SiO2. Typical isomerization catalysts are, for example, Pt/SAPO-11/Al2O3, Pt/ZSM-22/Al2O3, Pt/ZSM-23/Al2O3 and Pt/SAPO-11/SiO2.

Other factors, such as the concentration of water or undesired o intermediates, may also effect the composition and yields of the C4+ compounds, as well as the activity and stability of the condensation catalyst. In such event, the process may include a dewatering step that removes a portion of the water prior to the condensation reaction and/or the optional dehydration reaction, or a separation unit for removal of the undesired intermediates. For instance, a separator unit, such as a phase separator, extractor, purifier or distillation column, may be installed prior to the condensation step so as to remove a portion of the water from the reactant stream containing the intermediates. A separation unit may also be installed to remove specific intermediates to allow for the production of a desired product stream containing hydrocarbons within a particular carbon range, or for use as end products or in other systems or processes.

Thus, in one embodiment, the fuel blend produced by the processes described herein is a hydrocarbon mixture that meets the requirements for jet fuel (e.g., conforms with ASTM D1655). In another embodiment, the product of the processes described herein is a hydrocarbon mixture that comprises a fuel blend meeting the requirements for a diesel fuel (e.g., conforms with ASTM D975).

Yet in another embodiment of the invention, the $C_{2+}$ olefins are produced by catalytically reacting the intermediates in the presence of a dehydration catalyst at a dehydration temperature and dehydration pressure to produce a reaction stream comprising the $C_{2+}$ olefins. The $C_{2+}$ olefins comprise straight or branched hydrocarbons containing one or more carbon-carbon double bonds. In general, the $C_{2+}$ olefins contain from 2 to 8 carbon atoms, and more preferably from 3 to 5 carbon atoms. In one embodiment, the olefins comprise propylene, butylene, pentylene, isomers of the foregoing, and mixtures of any two or more of the foregoing. In another embodiment, the $C_{2+}$ olefins include $C_{4+}$ olefins produced by catalytically reacting a portion of the $C_{2+}$ olefins over an olefin isomerization catalyst. In an embodiment, a method of forming a fuel blend from a biomass feedstock may comprise a digester that receives a biomass feedstock and a digestive solvent operating under conditions to effectively remove nitrogen and sulfur compounds from said biomass feedstock and discharges a treated stream comprising a carbohydrate having less than 35% of the sulfur content and less than 35% of the nitrogen content based on the undigested biomass feedstock on a dry mass basis; a hydrogenolysis reactor comprising a hydrocatalytic treatment catalyst that receives the treated stream and discharges an oxygenated intermediate, wherein a first portion of the oxygenated hydrocatalytically treated mixture is recycled to the digester as at least a portion of the digestive solvent; a first fuels processing reactor comprising a dehydrogenation catalyst that receives a second portion of the oxygenated hydrocatalytically treated mixture and discharges an olefin-containing stream; and a second fuels processing reactor comprising an alkylation catalyst that receives the olefin-containing stream and discharges a liquid fuel.

The dehydration catalyst comprises a member selected from the group consisting of an acidic alumina, aluminum phosphate, silica-alumina phosphate, amorphous silica-alumina, aluminosilicate, zirconia, sulfated zirconia, tungstated zirconia, tungsten carbide, molybdenum carbide, titania, sulfated carbon, phosphated carbon, phosphated silica, phosphated alumina, acidic resin, heteropolyacid, inorganic acid, and a combination of any two or more of the foregoing. In one embodiment, the dehydration catalyst further comprises a modifier selected from the group consisting of Ce, Y, Sc, La, Li, Na, K, Rb, Cs, Mg, Ca, Sr, Ba, P, B, Bi, and a combination of any two or more of the foregoing. In another embodiment, the dehydration catalyst further comprises an oxide of an element, the element selected from the group consisting of Ti, Zr, V, Nb, Ta, Mo, Cr, W, Mn, Re, Al, Ga, In, Fe, Co, Ir, Ni, Si, Cu, Zn, Sn, Cd, P, and a combination of any two or more of the foregoing. In yet another embodiment, the dehydration catalyst further comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing.

In yet another embodiment, the dehydration catalyst comprises an aluminosilicate zeolite. In one version, the dehydration catalyst further comprises a modifier selected from the group consisting of Ga, In, Zn, Fe, Mo, Ag, Au, Ni, P, Sc, Y, Ta, a lanthanide, and a combination of any two or more of the foregoing. In another version, the dehydration catalyst further comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing.

In another embodiment, the dehydration catalyst comprises a bifunctional pentasil ring-containing aluminosilicate zeolite. In one version, the dehydration catalyst further comprises a modifier selected from the group consisting of Ga, In, Zn, Fe, Mo, Ag, Au, Ni, P, Sc, Y, Ta, a lanthanide, and a combination of any two or more of the foregoing. In another version, the dehydration catalyst further comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing.

The dehydration reaction is conducted at a temperature and pressure where the thermodynamics are favorable. In general, the reaction may be performed in the vapor phase, liquid phase, or a combination of both. In one embodiment, the dehydration temperature is in the range of about 100° C. to 500° C., and the dehydration pressure is in the range of about 0 psig to 900 psig. In another embodiment, the dehydration temperature is in the range of about 125° C. to 450° C., and the dehydration pressure is at least 2 psig. In another version, the dehydration temperature is in the range of about 150° C. to 350° C., and the dehydration pressure is in the range of about 100 psig to 800 psig. In yet another version, the dehydration temperature is in the range of about 175° C. to 325° C.

The $C_{6+}$ paraffins are produced by catalytically reacting the $C_{2+}$ olefins with a stream of $C_{4+}$ isoparaffins in the presence of an alkylation catalyst at an alkylation temperature and alkylation pressure to produce a product stream comprising $C_{6+}$ paraffins. The $C_{4+}$ isoparaffins include alkanes and cycloalkanes having 4 to 7 carbon atoms, such as isobutane, isopentane, naphthenes, and higher homologues having a tertiary carbon atom (e.g., 2-methylbutane and 2,4-dimethylpentane), isomers of the foregoing, and mixtures of any two or more of the foregoing. In one embodiment, the stream of $C_{4+}$ isoparaffins comprises of internally generated $C_{4+}$ isoparaffins, external $C_{4+}$ isoparaffins, recycled $C_{4+}$ isoparaffins, or combinations of any two or more of the foregoing.

The $C_{6+}$ paraffins will generally be branched paraffins, but may also include normal paraffins. In one version, the $C_{6+}$ paraffins comprises a member selected from the group consisting of a branched $C_{6-10}$ alkane, a branched $C_6$ alkane, a branched $C_7$ alkane, a branched $C_8$ alkane, a branched $C_9$ alkane, a branched $C_{10}$ alkane, or a mixture of any two or more of the foregoing. In one version, the C.sub.6+ paraffins comprise dimethylbutane, 2,2-dimethylbutane, 2,3-dimethylbutane, methylpentane, 2-methylpentane, 3-methylpentane, dimethylpentane, 2,3-dimethylpentane, 2,4-dimethylpentane, methylhexane, 2,3-dimethylhexane, 2,3,4-trimethylpentane, 2,2,4-trimethylpentane, 2,2,3-trimethylpentane, 2,3,3-trimethylpentane, dimethylhexane, or mixtures of any two or more of the foregoing.

The alkylation catalyst comprises a member selected from the group of sulfuric acid, hydrofluoric acid, aluminum chloride, boron trifluoride, solid phosphoric acid, chlorided alumina, acidic alumina, aluminum phosphate, silica-alumina phosphate, amorphous silica-alumina, aluminosilicate, aluminosilicate zeolite, zirconia, sulfated zirconia, tungstated zirconia, tungsten carbide, molybdenum carbide, titania, sulfated carbon, phosphated carbon, phosphated silica, phosphated alumina, acidic resin, heteropolyacid, inorganic acid, and a combination of any two or more of the foregoing. The alkylation catalyst may also include a mixture of a mineral acid with a Friedel-Crafts metal halide, such as aluminum bromide, and other proton donors.

In one embodiment, the alkylation catalyst comprises an aluminosilicate zeolite. In one version, the alkylation catalyst further comprises a modifier selected from the group consisting of Ga, In, Zn, Fe, Mo, Ag, Au, Ni, P, Sc, Y, Ta, a lanthanide, and a combination of any two or more of the foregoing. In another version, the alkylation catalyst further comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing.

In another embodiment, the alkylation catalyst comprises a bifunctional pentasil ring-containing aluminosilicate zeolite. In one version, the alkylation catalyst further comprises a modifier selected from the group consisting of Ga, In, Zn, Fe, Mo, Ag, Au, Ni, P, Sc, Y, Ta, a lanthanide, and a combination of any two or more of the foregoing. In another version, the alkylation catalyst further comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing. In one version, the dehydration catalyst and the alkylation catalyst are atomically identical.

The alkylation reaction is conducted at a temperature where the thermodynamics are favorable. In general, the alkylation temperature is in the range of about −20° C. to 300° C., and the alkylation pressure is in the range of about 0 psig to 1200 psig. In one version, the alkylation temperature is in the range of about 100° C. to 300° C. In another version, the alkylation temperature is in the range of about 0° C. to 100° C., and the alkylation pressure is at least 100 psig. In yet another version, the alkylation temperature is in the range of about 0° C. to 50° C. and the alkylation pressure is less than 300 psig. In still yet another version, the alkylation temperature is in the range of about 70° C. to 250° C., and the alkylation pressure is in the range of about 100 psig to 1200 psig. In one embodiment, the alkylation catalyst comprises a mineral acid or a strong acid and the alkylation temperature is less than ° C. In another embodiment, the alkylation catalyst comprises a zeolite and the alkylation temperature is greater than 100° C.

Aqueous Phase

FIG. 3 and the following description provide additional information more particularly related to embodiments employing an aqueous solvent mixture. In the embodiment shown, biomass 312 comprises at least a portion of a solid component generated according to aspects of embodiments of the invention, such as solid component 7 or 207 of FIGS. 1 and 2. Biomass 312 is introduced into digestion zone 314 where biomass 312 is contacted with digestive solvent 320. The treated biomass 316 contains soluble carbohydrates. The non-extractable solids may be optionally removed from the reaction as outlet stream 320. At least a portion of treated biomass 316 is catalytically reacted with hydrogen in hydrocatalytic zone 322 in the presence of a molecular hydrogen activating catalyst to produce a plurality of oxygenated intermediates 336. In some embodiments, treated biomass 316 may be optionally washed with any suitable solution before being fed to hydrocatalytic zone 322. If washed, a preferred solution in one embodiment is water.

At least a portion of oxygenated intermediates 336 can be catalytically reacted at reaction zone 330 to produce to form liquid fuel 332. Suitable processing reactions for reaction zone 330 include, but are not limited to, condensation reactions, oligomerization reaction, hydrogenation reaction, and any combination thereof. In some embodiments, the digestion reaction in zone 314, hydrocatalytic reaction in zone 322, and processing reactions in zone 330 can be conducted in a single step.

In a preferred embodiment, at least another portion of oxygenated intermediates can be recycled back to digestion zone 314 as part or all of digestive solvent 320. In the embodiment shown in FIG. 3, in addition or alternatively, a second portion of oxygenated intermediates 324 can be optionally treated at separation zone 326 before being recycled to digestion zone 314 as part of digestive solvent 320. Separation zone 326 can include elements adapted to separate oxygenated intermediates 324 into different component. For example, a suitable separator may include, but is not limited to, a phase separator, stripping column, extractor, or distillation column.

If separation zone 326 is used, at least a portion of the separated products 318, particularly higher polyols can be recycled back to digestion zone 314 as part or all of digestive solvent 320. The term "higher polyols" refers to a polyol with an oxygen to carbon ratio of 0.5 or more. Another portion of the separated products 328 can be directed to reaction zone 330 for contacting with a catalyst to form a liquid fuel. In one embodiment, optional separation zone 326 can also be used to remove some or all of the lignin from the oxygenated intermediate stream. The lignin may be passed out of separation stage 326 as a separate stream, for example as output stream 334.

In digestion zone 326, biomass 312 is contacted with digestive solvent 320 to effect a digestion reaction. The digestive solvent is preferably effective to digest lignins. Digestion zone 326 can comprise one or more digester(s).

Solubilization and hydrolysis can become complete at temperatures around 170 degrees C., aided by organic acids (e.g., carboxylic acids) formed from partial degradation of carbohydrate components. Some lignin can be solubilized before hemicellulose, while other lignin may persist to higher temperatures. At temperatures above about 120 degrees C., carbohydrates can degrade through a series of complex self-condensation reactions to form caramelans, which are considered degradation products that are difficult to convert to fuel products. In general, some degradation reactions can be expected with aqueous reaction conditions upon application of temperature, given that water will not completely suppress oligomerization and polymerization reactions.

In certain embodiments, the hydrolysis reaction can occur at a temperature between 20 degrees C. and 250 degrees C. and a pressure between 1 atm and 100 atm. An enzyme may be used for hydrolysis at low temperature and pressure. In embodiments including strong acid and enzymatic hydrolysis, the hydrolysis reaction can occur at temperatures as low as ambient temperature and pressure between 1 atm (100 kPa) and 100 atm (10,100 kPa).

Treated or digested biomass 316 is routed to hydrocatalytic reaction zone 322 to generate a plurality of oxygenated intermediates 336. At least a portion of oxygenated intermediates 336 can be catalytically reacted at reaction zone 330 to produce to form liquid fuel 332. Additional information for the hydrocataltyic reaction of zone 322 and processing reaction of zone 330 is provided above.

Organic Phase

FIG. 3 and the following description provide additional information more particularly related to embodiments employing an organic phase solvent mixture. Embodiments of the invention using an organic phase solvent can have an advantage using an organic-rich layer from thermocatalytic processing of biomass feedstocks recycled as solvent to digest biomass. The organic phase solvent is effective in preventing tar or heavy ends deposition during biomass digestion, and in assisting with the digestion via solvation, and recycle of carboxylic acid components. It can be used for thermocatalytic biofuels processes where the composition of intermediate products formed via hydrocatalytic treatment favors the formation of a significant fraction of organic phase components, as opposed to aqueous soluble components. Alternately, an externally formed organic hydrocarbon-rich solvent may be deliberately added to the reaction mixture. Use of an organic hydrocarbon-rich solvent can improve the solubilization of hydrogen into the reaction mixture relative to that which can be obtained with an aqueous phase solvent. It can also allows for convenient recycle of the organic solvent phase via liquid-liquid separation and decant, following biomass digestion and reaction. Physical separation of excess water and organic hydrocarbon-rich solvent after the digestion and reaction step can provide a process advantage by requiring less energy and equipment compared to the use of thermal distillation to separate solvents from water in a aqueous solvent-based process.

The organic-rich layer (organic phase) may be produced as intermediate products from hydrocatalytic treatment under organic phase hydrothermal conditions, and typically have a dielectric constant of greater than about 2, and are effective in assisting the digestion, hydrolysis and organic phase hydrocatalytic conversion of biomass-derived intermediates, via ability to solubilize water and ionic intermediates.

Suitable organic solvent mixtures will exhibit only partial miscibility when contacted with water, such that a second liquid phase is formed in the presence of water at least for some temperature between ambient (20° C.) and 300° C., and for at least a fraction of water between 0% and 100%. Partial miscibility enables at least some components of the solvent mixture to be conveniently recycled by liquid decant from a liquid-liquid or liquid-liquid-vapor contactor. The partially water miscible, organic solvent mixture will be comprised of one or more individual components which have only partial solubility in water, as referenced by C. L. Yaws, *Chemical Properties Handbook*, McGraw-Hill, NY (1999), Table 15-1. Some components of the mixture may be fully miscible or soluble with water at room temperature, for example propanol, ethanol, acetone, acetic acid, acetaldehyde, ethylene glycol, tetrahydrofuran, but the mixture must also contain a sufficient concentration of components containing only partial water miscibility such as n-butanol, n-pentanol, n-hexanol, n-octanol, aldehydes or ketones of $C_4$ or higher in carbon number, pentane, pentene and high molecular weight alkenes and alkanes, such that a second, hydrocarbon-rich organic liquid phase is formed. Propensity for individual components of the solvent mixture to partition between the hydrocarbon-rich organic phase and the excess water phase is described by their octanol-water partition coefficient (Yaws op cit.). Water will exhibit some solubility in the hydrocarbon-rich organic phase, typically above about 1 weight percent. Dielectric constant for the hydrocarbon-rich organic phase will be greater than about 2, but less than about 15, to comprise a solvent mixture of moderate polarity. The solvent provides for a finite solubility of carbohydrate intermediates such as glucose, fructose, mannose, xylose, xylitol, and sorbitol.

Water miscibility of organic hydrocarbon solvent mixtures is determined from empirical observation, and modeled using two-component activity coefficient models such as the Non Random Two Liquid (NTRL) model [Renon H., Prausnitz J. M., "Local Compositions in Thermodynamic Excess Functions for Liquid Mixtures", AIChE J., 14(1), S. 135-144, 1968]. While individual constituents of an organic hydrocarbon-rich phase may be fully miscible with water at ambient temperature, the mixture as an ensemble will form a phase which is not fully miscible, but forms a liquid-liquid interface with finite interfacial tension, between the organic hydrocarbon-rich phase, and the aqueous water-rich phase. Individual constituents will partition between the organic and aqueous phases, according to thermodynamic equilibrium. Prediction of miscibility may be based upon correlation of cohesive energy difference for individual components as correlated by the Hildebrand solubility parameter (Hildebrand, J. H. The Solubility of Non-Electrolytes; New York: Reinhold, 1936.], adapted to consider dispersion, polar, and hydrogen bonding components by Hanson (Hansen, Charles (2007). *Hansen Solubility Parameters: A user's handbook, Second Edition*. Boca Raton, Fla.: CRC Press]) An essential feature of the current inventive process is that digestion of biomass and hydrocatalytic reactions are conducted in the presence of a organic hydrocarbon rich phase which is not fully miscible with water and forms a second aqueous phase where water is present at 1:1 by mass ratio, at ambient temperature.

In one embodiment, biomass feedstock is contacted with an organic solvent having partial water miscibility to form a digested biomass stream. The digested biomass stream is contacted with hydrogen in the presence of a metal catalyst effective at activating molecular hydrogen (hydrocatalytic treatment) also referred as molecular hydrogen activating catalyst, to form a hydrocatalytically treated mixture that contains a plurality of hydrocarbon and oxygenated hydrocarbon molecules, where at least a portion of the organic solvent may be recycled from the organic phase of the intermediate product. The intermediate product (hydrocatalytically treated mixture) is phase separated by liquid-liquid separation, into an organic hydrocarbon-rich phase typically having a dielectric constant of greater than about 2, and a water phase comprising water soluble oxygenated hydrocarbons. At least a portion of the water phase containing the water soluble oxygenated hydrocarbons, and optionally at least a portion of the oxygenated hydrocarbon molecules in the organic phase, or both, are processed to form a fuel blend comprising higher hydrocarbons.

During digestion of biomass and hydrocatalytic reactions including reforming of carbohydrates to make hydrogen, if not already present, hydrogenation, hydrogenolysis, and hydrodeoxygenation, and other reactions, components such as alcohols or ketones greater than $C_4$ which are not fully water miscible across all concentration ranges, can form, to produce an organic phase. For this invention, the organic phase is recycled to a biomass digester and hydrocatalytic reactor, to effect "organic phase hydrocatalytic treatment". The organic phase may result directly from the selective formation of reaction products from hydrocatalytic reaction steps, including hydrogenation, hydrogenolysis, and hydrodeoxygenation. Further reaction of these intermediates via condensation and oligomerization reactions can also occur during hydrocatalytic processing, to render additional reaction intermediates which have on partial miscibility with water, and which can be used to form the organic phase solvent. This phase is separated via a liquid-liquid phase separator and decanter.

If separation of an aqueous rich phase is not observed directly in the reactor outlet as a result of the reaction product selectivities, reduction in temperature after reaction can lead to formation of separate organic-rich and aqueous phases, via "Temperature induced phase separation" (TIPS). Alternately, an external solvent may be added (alkane, aromatic) that is not fully miscible with water, which can lead to a second phase forming in the liquid-liquid separator (Concentration Induced Phase Separation), insuring the ability to recycle an organic-rich solvent phase. If the water concentration is not sufficient to induce formation of a second liquid phase after reaction, water may be added to extract a portion of the water soluble components, and induce a phase separation to enable recycle of an organic hydrocarbon-rich phase.

In one preferred embodiment, the digestion of biomass and hydrocatalytic reactions are conducted in the presence of a single, organic phase, with no separate aqueous phase observed until after the reaction step. This may be facilitated by recycling light oxygenated solvents from the aqueous coproduct stream (ethanol, isopropanol, propanol, acetone). Use of flash distillation to recycle light (<C4) oxygenated solvents will enable the water and polyol components of digested biomass to be dissolved into the recycle organic solvent mixture, without forming a second aqueous rich phase until cool down to induce TIPS, extraction with excess water, or flash of the solvent mixture to remove the miscibilizing light oxygenated solvent.

In the invention, it is important to recycle an "organic phase" to effect digestion of biomass and act as solvent for the hydrocatalytic reactions, where "organic phase" is defined as a phase where the ratio of water to organic components is less than 1:1, and where two liquid phases are formed upon equilibrating at ambient temperature, if the mass ratio of organic solvent components to water is greater than 1:1. Equilibration entails intimate mixing or other means of contacting to assure that thermodynamic equilibrium is obtained throughout the mixture, and across any phase boundaries which may form.

Figure 4:
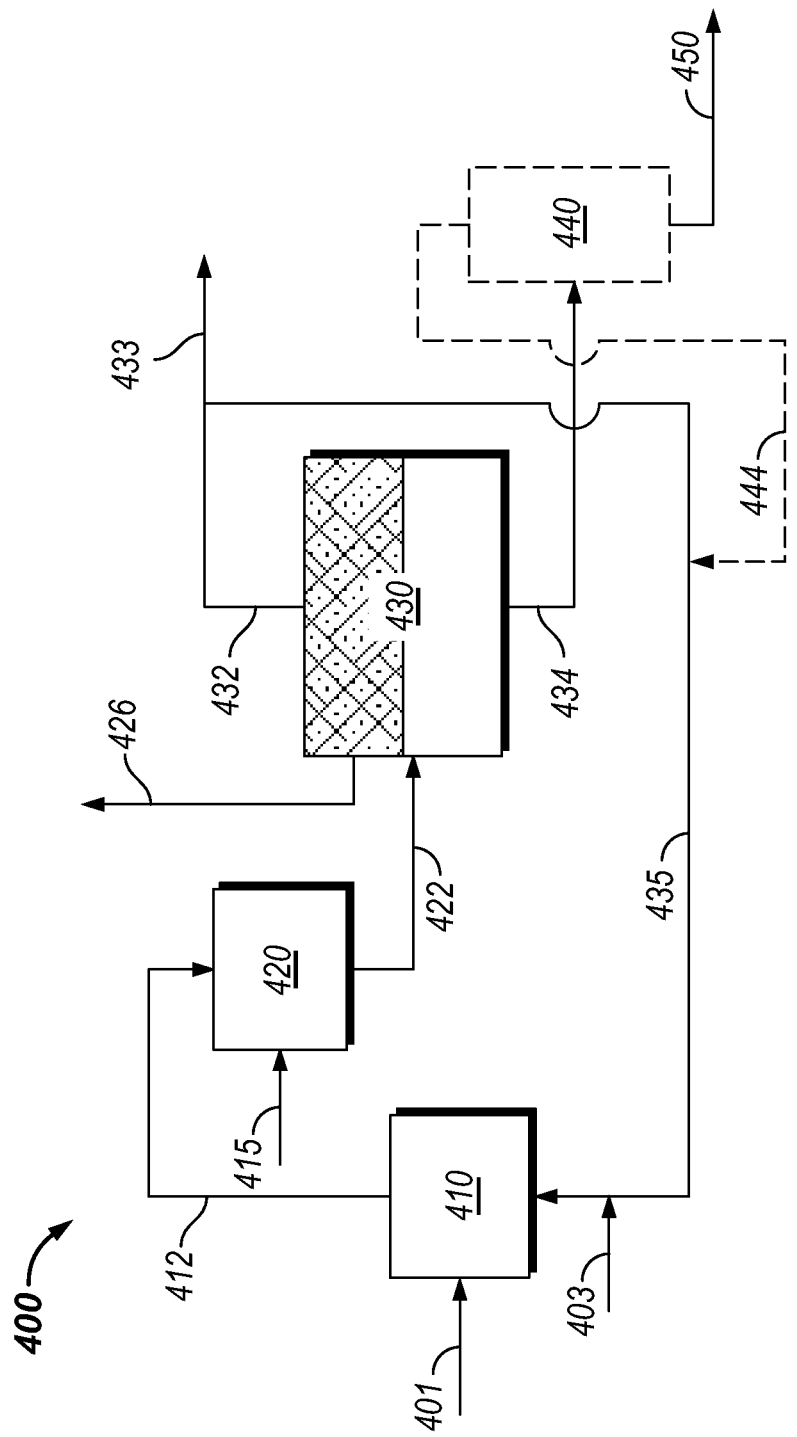
FIG. 4 is a diagram of another embodiment to convert a solid component to a higher hydrocarbon according to certain aspects of the present invention.

FIG. 4 schematically describes one embodiment of the formation and recycle of the organic phase. FIG. 4 shows optional flash distillation of the aqueous coproduct stream to recycle a light miscibilizing solvent to blend with the organic phase recycle stream. Any water phase and organic phase liquid-liquid separation technique can be used. The phase may phase form directly in the reactor outlet as a result of the reaction product selectivities, reduction in temperature after reaction via "Temperature induced phase separation" (TIPS), use of liquid-liquid coalescers, or by adding external solvent (alkane, aromatic) that is not fully miscible with water, which can lead to a second phase forming in the liquid-liquid separator (Concentration Induced Phase Separation) such as described in detail in "Liquid-Liquid Extraction Using the Composition-Induced Phase Separation Process," Ind. Eng. Chem. Res. 1996, 35, 2360-2368. In a preferred embodiment, separation of an organic rich layer is achieved via cooling prior to the liquid-liquid separator (TIPS), or addition of a water-rich stream as "water extractant" (CIPS).

In such embodiment, 400, biomass feedstock 401 is provided to digestion system 410 that may have one or more digester(s), whereby the biomass is contacted with an organic solvent exhibiting partial miscibility with water at 25° C. thereby forming a digested biomass stream. As mentioned, a minimum of about one weight percent water is required in the digester, to effect these reactions. Water is in most cases present in the biomass feed, and is also solubilized at an equilibrium concentration in the organic solvent mixture recycled from the liquid-liquid phase separation and decant (430).

The organic solvent may contain make-up solvent 403 and recycled organic hydrocarbon-rich phase 435. Water is generally present in the organic phase solvent mixture, at a concentration of less than 50 weight percent, most typically less than 15 weight percent. Contact of the organic solvent with the biomass feedstock in digestive system 410 results in formation of digested biomass stream 412. At least a portion of the digested biomass stream 412 is fed to a organic phase hydrocatalytic treatment system 420 whereby the digested biomass is catalytically reacted with hydrogen (optionally external hydrogen may be added 415) in the presence of a hydrocatalytic treatment metal catalyst capable of activating molecular hydrogen, to produce a hydrocatalytically treated mixture 422 exiting the hydrocatalytic treatment system 420, containing at least one partial water miscible molecule such as, for example, n-butanol, n-pentanol, n-hexanol, n-octanol, aldehydes or ketones of $C_4$ or higher in carbon number, pentane, pentene and high molecular weight alkenes and alkanes, and the like along with other water-miscible small molecules and oxygenated molecules such as ethylene glycol, and any added or formed aromatic or hydrocarbon solvents such as toluene, benzene, or alkanes. A portion of the hydrocatalytically treated mixture 422 may be directly recycled to digester 410, to control residence time and concentrations in digestion and reaction steps. The portion of the hydrocatalytically treated mixture 422 that is not optionally recycled, is phase separated into an organic phase and water phase by liquid-liquid separation 430 to form an organic hydrocarbon-rich phase stream 432 (organic phase) and an aqueous phase stream 434. A portion (first portion) of the organic phase is recycled 435 to the digestor(s) in digestion system 410.

Optionally, a second portion 433 of the organic phase may be further processed to a liquid fuel blend as described above.

Light oxygenated solvents (ethanol, isopropanol, propanol, acetone) with volatility greater than water, and present in aqueous hydrocatalytically treated mixture 434 are optionally flash distilled 440 and recycled as stream 444, to further increase the solvent strength of the organic recycle stream. In one embodiment, at least a portion of the aqueous phase stream 434 containing oxygenated intermediates may also pass to further processing stage as described above. For example, aqueous bottoms stream 450 is optionally further processed to produce higher hydrocarbons, optionally together with the organic hydrocatalytically treated mixture 433.

In one embodiment (not shown), a fraction of the hydrocatalytically treated mixture stream 422 may optionally be directly recycled to digestion system 410 to provide solvent for hydrolysis and dilution the digested biomass stream 412. In some embodiments, system 400 may incorporate a separation stage similar to separation stage 326 of FIG. 3, in which case the corresponding descriptions are equally applicable to system 400. In those embodiments, an outlet stream from the separation stage can also be used to remove some or all of the lignin from the oxygenated hydrocatalytically treated mixture. The lignin may be passed out of the separation stage as a separate stream, for example as output stream.

To facilitate a better understanding of embodiments the present invention, the following examples of certain aspects of some embodiments are given. In no way should the following examples be read to limit, or define, the entire scope of the invention.

ILLUSTRATIVE EMBODIMENTS

Example A

Biomass Preparation

In this example, various samples of fresh chopped sorghum are mixed with a variety of added components as listed in Table A.1 and are stored in a silage bag for about 20 days. The particular additives and respective addition rates are shown in Table A.2.

TABLE A.1

| 2011 Experiments | WITH ACID |
|---|---|
| Experiment # | 1 |
| estimated mass | 450 kg |
| Moisture Content | 76% |
| Storage Method | Silage bag |
| Yeast | Lallemand Liquid Yeast |
| bacterial inhibitor | Lactrol |
| Enzyme | Novozymes Cellic CTec2 |
| Chop size | 3 mm |
| Result (gallons Ethanol/initial dry metric tonne) | 50 |
| Days in Storage | ~20 |

TABLE A.2

| ADDITIVE | Rates |
|---|---|
| LACTROL | 3.2 g/wet ton |
| Lallemand Stabilized Liquid Yeast | 18 fl oz/wet ton |
| Novozymes Cellic CTec2 | 20 fl oz/wet ton |
| 9.3% Concentrated Sulfuric Acid | 3.8 L/wet ton |

VOC Recovery

The VOCs from the prepared biomass material of this example were recovered using a GEA SSD™ as the solventless recovery unit. Table A.3 below provides certain properties of (i) the prepared biomass material fed into the solventless recovery unit, (ii) the solid component exiting the solventless recovery unit, and (iii) the operating conditions of the solventless recovery unit.

| | Sample |
|---|---|
| | Feed composition |
| Liquid in Feed (%) | 80.2% |
| | Solid component |
| Liquid in Solid component (%) | 60.21% |
| Solid component Temperature (F.) | 87 |
| | Operating Conditions |
| Heater Temperature (F.) | 552 |
| Feed Rate (lb/min.) | 5.30 |
| Evaporation Rate (lb/min) | 2.71 |
| Saturation Temperature (F.) | 222 |
| Solid component production rate (lb/min.) | 2.55 |
| Vapor Temperature at Inlet (F.) | 423 |
| Exhaust Temperature (F.) | 235 |
| Operating Pressure (psig) | 3 |

Further Processing: Digestion and Hydrocatalytic Reactions

Aqueous phase digestion and reforming reactions were conducted in a 75-ml stirred multiple reactor system (Parr 5000 Series), which was charged with 20.0 grams of 50% ethanol/de-ionized water solvent, 0.0996 grams of potassium carbonate buffer, and 0.3020 grams of nickel-oxide promoted cobalt molybdate catalyst DC-2534, containing 1-10% cobalt oxide and molybdenum trioxide (up to 30 wt %) on alumina, and less than 2% nickel, obtained from Criterion Catalyst & Technologies L.P., and sulfided by the method described in US2010/0236988 Example 5.

2.7007 grams of the solid component of Example A at 62% moisture were added, before pressuring with 52.7 bar of hydrogen with stirring at 600 rpm via a 1.5 cm×0.75 cm stir bar. The reactor was heated to 190° C. for 1 hour, before increasing to 250° C. and holding for four hours, to complete a five hour total cycle.

At the end of the reaction, the reactor content was filtered via a vacuum filter flask using Whatman GF/A filter to recover catalyst and undigested solid component. Recovered solids were oven dried overnight at 90° C. to assess the extent of digestion of biomass and determine a percent "digested." As used herein, "digested" or "digestion" means soluble enough to pass through the filter paper after cooling to room temperature. Results indicated 80% digestion, meaning 80% of the solid component changed into liquid soluble products that can be converted to intermediate oxygenated products.

The aqueous product was analyzed by gas chromatography ("DB5-ox method") using a 60-m×0.32 mm ID DB-5 column of 1 μm thickness, with 50:1 split ratio, 2 ml/min helium flow, and column oven at 40° C. for 8 minutes, followed by ramp to 285° C. at 10° C./min, and a hold time of 53.5 minutes. The injector temperature was set at 250° C., and the detector temperature was set at 300° C.

The gas chromatography showed a range of products in the reactor content were observed with volatility greater than C6 sugar alcohol sorbitol. Tetrahydrofurfural alcohol was the dominant product formed (45% by weight of products formed), with 1,2-propylene glycol formed as a secondary product (14% by weight of products formed). These the fraction of products that can be further blended into useful fuels. In addition, the GC measured products indicated a selectivity of 74% (of the 80% digested material) to products with volatility greater than sorbitol (C6 monomer), relative to the dry mass content of the digested portion of the biomass initially charged in the reactor.

Additional products formed, as analyzed by GC-mass spectrometry, included ethyl proprionate, 4-methyl-2-pentanol, ethylene glycol, butanediol, cyclohexanone, 2-ethyl cyclohexanone, ethyl phenol, and methoxypropyl phenol. The results of this example demonstrate digestion with concerted hydrodeoxygenation (HDO) reaction in the presence of an aqueous phase solvent and hydrogenolysis catalyst.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

We claim:

1. A method for processing a biomass material comprising:
    introducing a biomass material to a compartment of a solventless recovery system, wherein the biomass material contains one or more volatile organic compounds;
    contacting the biomass material with a superheated vapor stream in the compartment to vaporize at least a portion of an initial liquid content in the biomass material, said superheated vapor stream comprising at least one volatile organic compound;
    separating a vapor component and a solid component from the heated biomass material, said vapor component comprising at least one volatile organic compound;
    retaining at least a portion of the vapor component for use as part of the superheated vapor stream;
    discharging the solid component from the solventless recovery system;
    contacting at least a portion of the solid component with a digestive solvent to form a digested biomass stream comprising carbohydrates;
    contacting the digested biomass stream with molecular hydrogen in the presence of a molecular hydrogen activating catalyst to form a hydrocatalytically treated mixture comprising a plurality of oxygenated hydrocarbon molecules, wherein a first portion of the oxygenated hydrocarbon molecules is recycled to form at least part of the digestive solvent; and
    processing at least a second portion of the oxygenated hydrocarbon molecules to form a fuel blend.

2. The method of claim 1 wherein the fuel blend comprises at least one composition selected from the group consisting of: a fuel additive, a gasoline fuel, a diesel fuel, and a jet fuel.

3. The method of claim 1 wherein the processing of at least a second portion of the oxygenated intermediates comprises contacting at least the second portion of the oxygenated intermediates with a hydrogenation catalyst to form the fuel blend.

4. The method of claim 3 wherein the fuel blend comprises at least one additive selected from the group consisting of: a saturated alcohol, a saturated polyol, and a saturated hydrocarbon.

5. The method of claim 1 wherein the processing of at least a second portion of the oxygenated intermediates comprises contacting at least the second portion of the oxygenated intermediates with a condensation catalyst to form the fuel blend, wherein the fuel blend comprises a gasoline fuel.

6. The method of claim 1 wherein the processing of at least a second portion of the oxygenated intermediates comprises contacting at least the second portion of the oxygenated intermediates with an acid catalyst to form at least some olefins; and contacting the olefins with an oligomerization catalyst to form the fuel blend.

7. The method of claim 1 wherein the biomass material introduced to the compartment is obtained from a solid state fermentation process of a harvested crop.

8. The method of claim 7 wherein the crop is selected from the group consisting of sorghum, sugar cane, corn, tropical corn, sugar beet, energy cane, and any combination thereof.

9. The method of claim 1 wherein the compartment comprises a cylindrical body in a shape of a loop within which the superheated vapor stream flows.

10. The method of claim 1 wherein the separating step is achieved using a cyclone separating unit coupled to the compartment, wherein the cyclone separating unit is configured to discharge the separated solid component from the compartment.

11. The method of claim 1 wherein the biomass is generated by adding to the biomass at least one additive, wherein said at least one additive comprises a microbe, and optionally, an acid and/or an enzyme; and storing the biomass material for at least about 24 hours in a storage facility.

12. The method of claim 1 wherein the biomass has an average size distribution of about 3 mm to about 80 mm.

13. The method of claim 1 further comprises feeding at least a portion of the solid component from the solventless recovery system directly to the hydrocatalytic treatment.

14. A method for processing a biomass material comprising:
    contacting a solid component of a biomass material with a digestive solvent to form a digested biomass stream, wherein the solid component is generated by a method comprising:
        introducing a biomass material to a compartment of a solventless recovery system, wherein the biomass material contains one or more volatile organic compounds;
        contacting the biomass material with a superheated vapor stream in the compartment to vaporize at least a portion of an initial liquid content in the biomass material, said superheated vapor stream comprising at least one volatile organic compound;
        separating a vapor component and a solid component from the heated biomass material, said vapor component comprising at least one volatile organic compound;

retaining at least a portion of the vapor component for use as part of the superheated vapor stream; and discharging the solid component from the solventless recovery system;

contacting the digested biomass stream with molecular hydrogen in the presence of a molecular hydrogen activating catalyst to form a hydrocatalytically treated mixture comprising a plurality of oxygenated hydrocarbon molecules, wherein a first portion of the oxygenated hydrocarbon molecules is recycled to form at least part of the digestive solvent; and processing at least a second portion of the oxygenated hydrocarbon molecules to form a fuel blend.

15. The method of claim 14 wherein the fuel blend comprises at least one composition selected from the group consisting of: a fuel additive, a gasoline fuel, a diesel fuel, and a jet fuel.

16. The method of claim 14 wherein the processing of at least a second portion of the oxygenated intermediates comprises contacting at least the second portion of the oxygenated intermediates with a hydrogenation catalyst to form the fuel blend.

17. The method of claim 16 wherein the fuel blend comprises at least one additive selected from the group consisting of: a saturated alcohol, a saturated polyol, and a saturated hydrocarbon.

18. The method of claim 1 wherein the biomass is generated by adding to the biomass at least one additive, wherein said at least one additive comprise a microbe, and optionally, an acid and/or an enzyme; and storing the biomass material for at least about 24 hours in a storage facility.

19. The method of claim 14 wherein at least a portion of the solid component is discharged from the solventless recovery system to the hydrocatalytic treatment.

20. The method of claim 1 wherein the digestive solvent comprises an organic solvent having partial miscibility with water at 25 degrees C. and the organic solvent to water mass ratio in the digested biomass stream is greater than 1:1, the method further comprising:

phase separating the hydrocatalytically treated mixture, by liquid-liquid separation, into an organic hydrocarbon-rich phase and a water phase; recycling at least a portion of the organic hydrocarbon-rich phase to form at least a portion of the organic solvent; and processing at least a portion of the water phase and/or organic hydrocarbon-rich phase, to form a plurality of higher hydrocarbons.

21. A method for processing a biomass material comprising:

introducing a prepared biomass material to a compartment of a recovery system, wherein the biomass material contains at least one volatile organic compound;

contacting the prepared biomass material with a superheated vapor stream in the enclosed compartment;

removing less than 99% of the at least one volatile organic compound in the stored prepared biomass material to provide a vapor component;

retaining at least a portion of the vapor component for use as part of the superheated vapor stream; and releasing from the compartment at least a portion of the prepared biomass material after removal of the at least one volatile organic compound to provide a solid component;

contacting at least a portion of the solid component with a digestive solvent to form a digested biomass stream comprising carbohydrates;

contacting the digested biomass stream with molecular hydrogen in the presence of a molecular hydrogen activating catalyst to form a hydrocatalytically treated mixture comprising a plurality of oxygenated hydrocarbon molecules, wherein a first portion of the oxygenated hydrocarbon molecules is recycled to form at least part of the digestive solvent; and processing at least a second portion of the oxygenated hydrocarbon molecules to form a fuel blend.

22. The method of claim 21, wherein the solid component contains liquid in a range of about 30 wt % to about 70 wt %.

23. The method of claim 21, wherein the vapor component contains volatile organic compounds in a range of about 1 wt % and about 50 wt % ethanol.

24. The method of claim 21, wherein the solid component exiting the recovery system has a temperature of less than about 50° C.

25. The method of claim 21 further comprising operating the recovery system at a pressure in a range of 3 psig to about 60 psig.

26. The method of claim 21 comprising removing in a range of 50% to 95% of the at least one volatile organic compound in the prepared biomass material.

27. The method of claim 21 wherein the prepared biomass is generated by adding a microbe to the biomass and storing the biomass material with the microbe for at least about 24 hours in a storage facility.

* * * * *